(12) United States Patent
Brose

(10) Patent No.: US 8,637,554 B2
(45) Date of Patent: Jan. 28, 2014

(54) METHODS FOR TREATING THYROID CANCER

(75) Inventor: Marcia S. Brose, Bryn Mawr, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 807 days.

(21) Appl. No.: 12/436,957

(22) Filed: May 7, 2009

(65) Prior Publication Data

US 2009/0311175 A1  Dec. 17, 2009

Related U.S. Application Data

(60) Provisional application No. 61/071,598, filed on May 7, 2008, provisional application No. 61/114,423, filed on Nov. 13, 2008.

(51) Int. Cl.
*A61K 31/44* (2006.01)
*A61K 31/17* (2006.01)

(52) U.S. Cl.
USPC .......................................... 514/350; 514/596

(58) Field of Classification Search
None
See application file for complete search history.

(56) References Cited

U.S. PATENT DOCUMENTS

| 2005/0048533 | A1* | 3/2005 | Sidransky et al. ................ 435/6 |
| 2007/0015837 | A1 | 1/2007 | Kun et al. |
| 2007/0135387 | A1 | 6/2007 | Michaelides et al. |
| 2007/0191604 | A1 | 8/2007 | Cooper et al. |
| 2007/0281955 | A1 | 12/2007 | Lapierre et al. |

FOREIGN PATENT DOCUMENTS

WO  WO 2007/087245  8/2007

OTHER PUBLICATIONS

Ball et al. J. Clin. Endocrinol. Metab., 2007, vol. 92, pp. 4712-4718.*
Kim et al. Mol. Cancer Ther., 2007, vol. 6, pp. 1785-1792.*
Kurebayashi et al. Cancer Chemother. Pharmacol., 2006, vol. 58, pp. 460-470.*
Salvatore et al. Clin. Cancer Res., 2006, vol. 12, pp. 1623-1629.*
Registry Information of Sorafenib, acccessed Feb. 7, 2012.*
Kloos et al. Journal of Clinical Oncology, 2006 ASCO Meeting Proceedings, vol. 24, No. 18S (Jun. 20 Supplement), 2006, p. 5534.*
Wilhelm et al. Nature Reviews, Oct. 2006, vol. 5, pp. 835-844.*
Schlumberger et al. NEJM, 1998, vol. 338, No. 5, pp. 297-306.*
Elias et al. Clin. Nucl. Med., 2006, vol. 31, pp. 517-519.*
Liu et al. J. Clin. Endocrinol. Metab., 2007, vol. 92, pp. 4686-4695.*
Hoftijzer et al. European Journal of Endocrinology, 2009, vol. 161, pp. 923-931.*
Mannavola et al. J. Clin. Endocrinol. Metab., 2007, vol. 92, No. 9, pp. 3531-3534.*
"Kinase List". Jul. 2007, Accessed from http://phospho.elm.eu.org/kinase_list.pdf on Feb. 3, 2012.*
Fergal et al. Annals of Internal Medicine, Apr. 1, 2008, vol. 148, No. 7, p. 567.*
Liu et al. Clin. Cancer Res., Feb. 2007, vol. 13, No. 4, pp. 1341-1349.*
Buchwald et al., "Long-term, continuous intravenous heparin administration by an implantable infusion pump in ambulatory patients with recurrent venous thrombosis", Surgery 1980, p. 507.
Saudek et al., "A preliminary trial of the programmable implantable medication system for insulin delivery", The New England Journal of Medicine, vol. 321, No. 9, p. 574-579, 1989.
Langer, "New methods of drug delivery", Science, vol. 249, p. 1527-1533, 1990.
Katre et al., "Chemical modification of recombinant interleukin 2 by polyethylene glycol increases its potency in the murine Meth A sarcoma model" Proc. Natl. Acad. Sci., vol. 84, pp. 1487-1491, 1987.
Goodson et al., Medical applications of controlled release, vol. 2, p. 115-138, 1984.

\* cited by examiner

*Primary Examiner* — James D Anderson
(74) *Attorney, Agent, or Firm* — Mark S. Cohen; Pearl Cohen Zedek Latzer Baratz LLP

(57) ABSTRACT

The invention provides methods for enhancing iodine absorption in a thyroid in a subject and treating thyroid cancer by administering to the subject a composition which includes a multi-kinase inhibitor. Furthermore, the invention provides methods for improving a medical diagnostic procedure based on radioactive iodine in a subject by administering to the subject a composition comprising a multi-kinase inhibitor.

25 Claims, 13 Drawing Sheets

METHODS FOR TREATING THYROID CANCER

CROSS REFERENCE TO RELATED APPLICATIONS

This application claims priority to U.S. Provisional Patent Applications 61/071,598, filed May 7, 2008 and 61/114,423, filed Nov. 13, 2008, both of which are incorporated herein by reference in their entirety.

FIELD OF THE INVENTION

The invention relates to methods for treating thyroid cancer in a subject. Specifically, the invention relates to enhancing iodine absorption in thyroid by administering multi-kinase inhibitors, and thereby treating thyroid cancer.

BACKGROUND OF THE INVENTION

Thyroid cancer refers to any of five kinds of malignant tumors of the thyroid gland: papillary, follicular, hürthle cell, medullary and anaplastic. Papillary and follicular, and hürthle cell tumors are the most common: they grow slowly, may recur, but are generally not fatal in patients under 45 years of age. Medullary tumors have a good prognosis if restricted to the thyroid gland and a poorer prognosis if metastasis occurs. Anaplastic tumors are fast-growing and respond poorly to all therapies.

Thyroid nodules are diagnosed by ultrasound guided fine needle aspiration (USG/FNA) or frequently by thyroidectomy (surgical removal and subsequent histological examination). As thyroid cancer can take up iodine, radioactive iodine is commonly used to follow and treat thyroid carcinomas, followed by TSH suppression by thyroxine therapy.

Thyroid cancer is the most common endocrine malignancy, with 33,500 new cases of thyroid cancers estimated to be diagnosed in the U.S. in 2008. Differentiated thyroid carcinoma comprises 90% of all cases. Once thyroid cancer metastasizes to distant sites and is no longer amenable to radioactive iodine therapy or surgery, expected survival declines rapidly. The only FDA-approved therapy for these patients is doxorubicin.

To date, no effective therapy is available for treating metastatic cancer that is not amenable to radioactive iodine therapy or surgery. Accordingly, a need exists for improved methods and compositions for treating thyroid cancer.

SUMMARY OF THE INVENTION

In one embodiment, the invention provides a method of treating a thyroid cancer in a subject, comprising the step of enhancing iodine absorption in a thyroid in said subject by administering to said subject a composition comprising a multi-kinase inhibitor, thereby treating said thyroid cancer in said subject. In one exemplary embodiment, said thyroid cancer is an iodine non avid metastatic thyroid cancer.

In another embodiment, the invention provides a method of treating a thyroid cancer in a subject, comprising the step of enhancing iodine absorption in a thyroid in said subject by administering to said subject a composition comprising sorafenib, thereby treating said thyroid cancer in said subject.

In another embodiment, the invention provides a method of enhancing iodine absorption in a thyroid in a subject, comprising the step of administering to said subject a composition comprising a multi-kinase inhibitor, thereby enhancing iodine absorption in the thyroid in said subject.

In another embodiment, the invention provides a method of enhancing iodine absorption in a thyroid in a subject, comprising the step of administering to said subject a composition comprising sorafenib, thereby enhancing iodine absorption in the thyroid in said subject.

In another embodiment, the invention provides a method of treating thyroid cancer in a subject before or after primary treatment, the method comprising administering to a subject in need of adjuvant or neoadjuvant therapy for thyroid cancer, a therapeutically effective amount of a composition comprising a multi-kinase inhibitor.

In another embodiment, the invention provides a method of treating thyroid cancer in a subject before or after primary treatment, the method comprising administering to a subject in need of adjuvant or neoadjuvant therapy for thyroid cancer, a therapeutically effective amount of a composition comprising sorafenib.

In another embodiment, the invention provides a method for providing a medical diagnosis based on radioactive iodine in a subject, comprising the step of administering to said subject a composition comprising a multi-kinase inhibitor, thereby providing said medical diagnosis in said subject.

In another embodiment, the invention provides a method for providing a medical diagnosis based on radioactive iodine in a subject, comprising the step of administering to said subject a composition comprising sorafenib, thereby providing said medical diagnosis in said subject.

In another embodiment, the invention provides a composition comprising an effective amount of a multi-kinase inhibitor for enhancing iodine absorption in a subject.

In another embodiment, the invention provides a composition comprising an effective amount of sorafenib for enhancing iodine absorption in a subject.

In another embodiment, the invention provides a composition comprising a multi-kinase inhibitor and iodine.

In another embodiment, the invention provides a composition comprising sorafenib and iodine.

Other features and advantages of the present invention will become apparent from the following detailed description examples and figures. It should be understood, however, that the detailed description and the specific examples while indicating preferred embodiments of the invention are given by way of illustration only, since various changes and modifications within the spirit and scope of the invention will become apparent to those skilled in the art from this detailed description.

rose steadily after an initial deline to 25% baseline levels Response A). In contrast, patient 3 also initially dropped in both tumor size and sTG levels, but a steady increase in sTG was followed by increased tumor size (Response B). After 15 cycles, patient 3 was discontinued form the trial on the basis of progressive disease, while patient 5 continues to maintain his PR.

Figure 5:
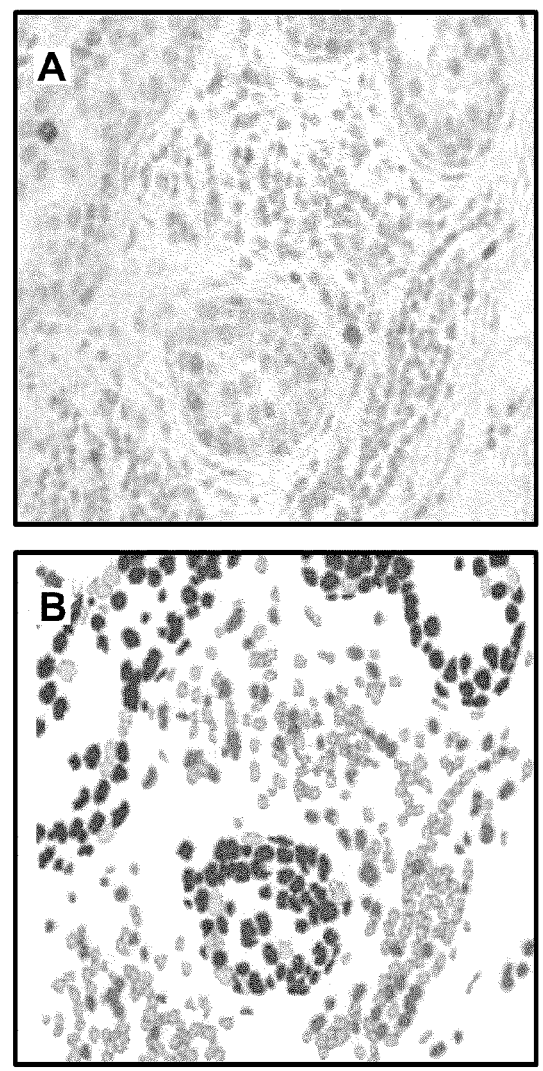
Figure 5:
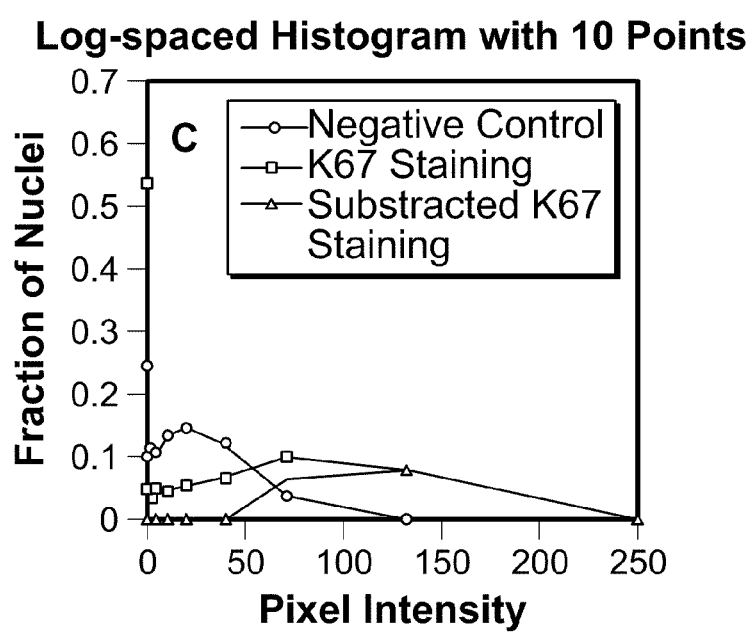

FIG. 5 shows P-ERK expression from metastatic PTC lesions from a patient prior to (A), and after one week of sorafenib (B). The number of nuclei as well as the intensity of staining occurring in the two samples was determined quantitatively (C).

Figure 6:
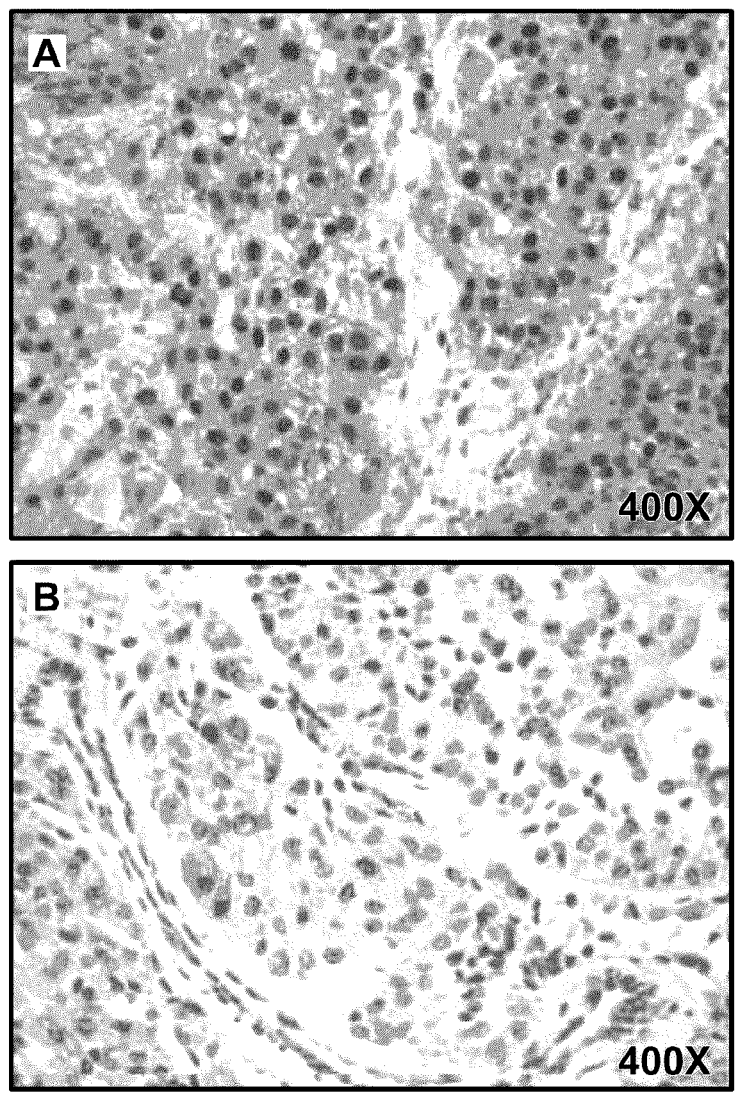
Figure 6:
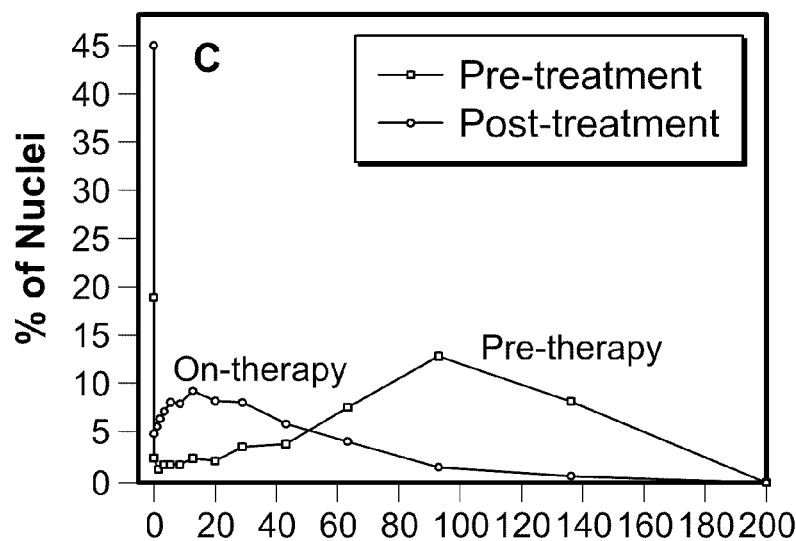

FIG. 6 shows P-ERK expression from metastatic PTC lesions from a patient prior to (A), and after one week of sorafenib (B). The number of nuclei as well as the intensity of staining occurring in the two samples can be determined quantitatively (C).

Figure 7:
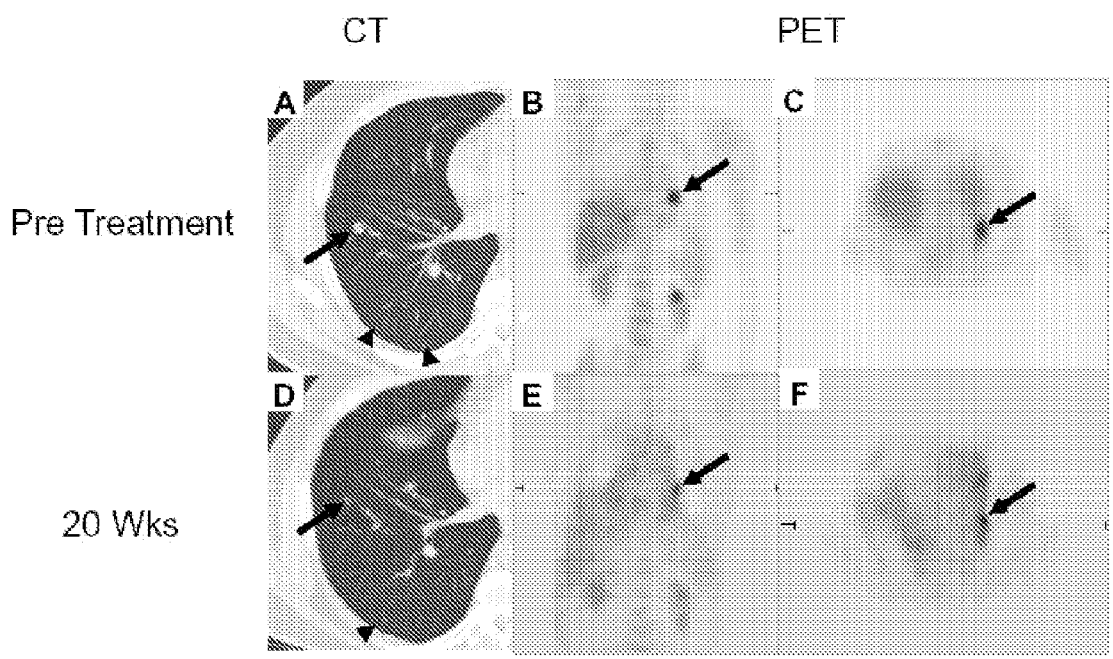

FIG. 7 shows PET and CT scans obtained prior to beginning therapy and after one year of sorafenib treatment.

Figure 8:
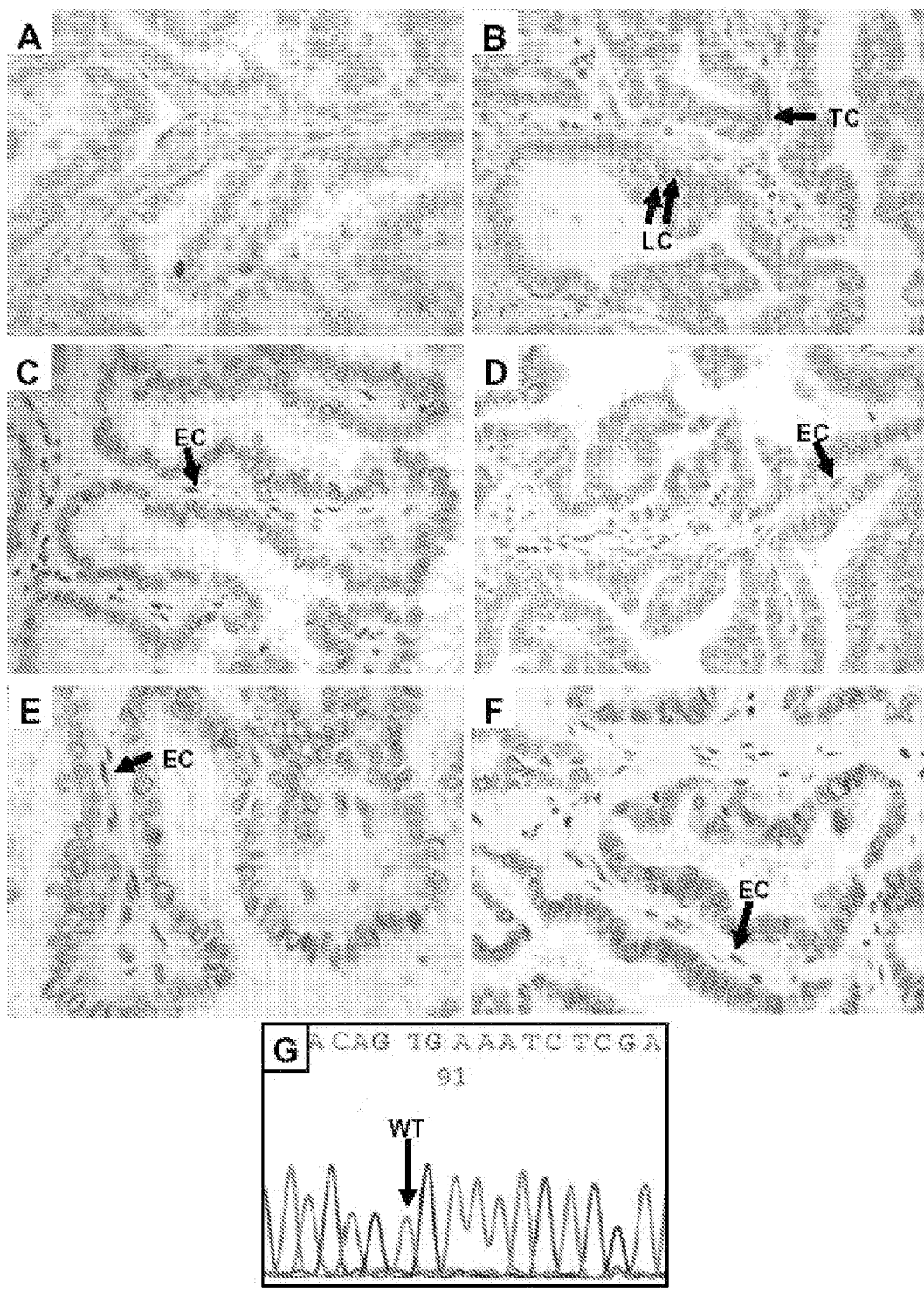

FIG. 8 shows immunohistochemical micrographs of ECs and TCs from patient 1 for the detection of Ki-67, p-ERK, and P-AKT. Ki-67 staining in ECs and TCs in pre-treatment tissue and two weeks of treatment (8a and 8b). p-ERK staining in ECs and TCs in pre-treatment tissue and two weeks of treatment (8c and 8d). P-AKT staining in ECs and TCs in pre-treatment tissue and two weeks of treatment (8e and 8f). The genotype of this tumor-BRAF$^{wt}$ (8g)

Figure 9:
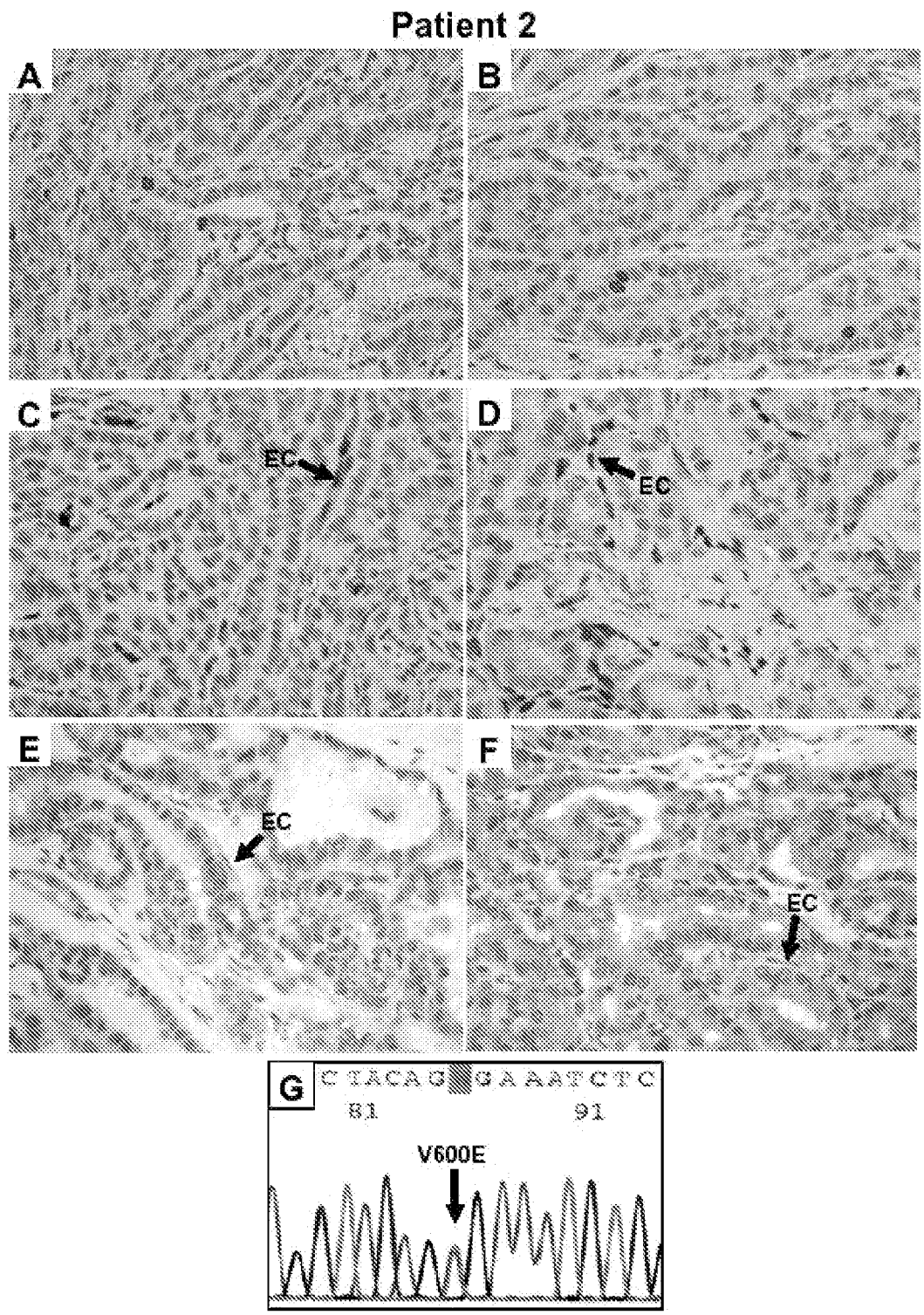

FIG. 9 shows immunohistochemical micrographs of ECs and TCs from patient 2 for the detection of Ki-67, p-ERK, and P-AKT. Ki-67 staining in ECs and TCs in pre-treatment tissue and two weeks of treatment (9a and 9b). p-ERK staining in ECs and TCs in pre-treatment tissue and two weeks of treatment (9c and 9d). P-AKT staining in ECs and TCs in pre-treatment tissue and two weeks of treatment (9e and 9f). The genotype of this tumor-BRAF$^{wt}$ (9g).

Figure 10:
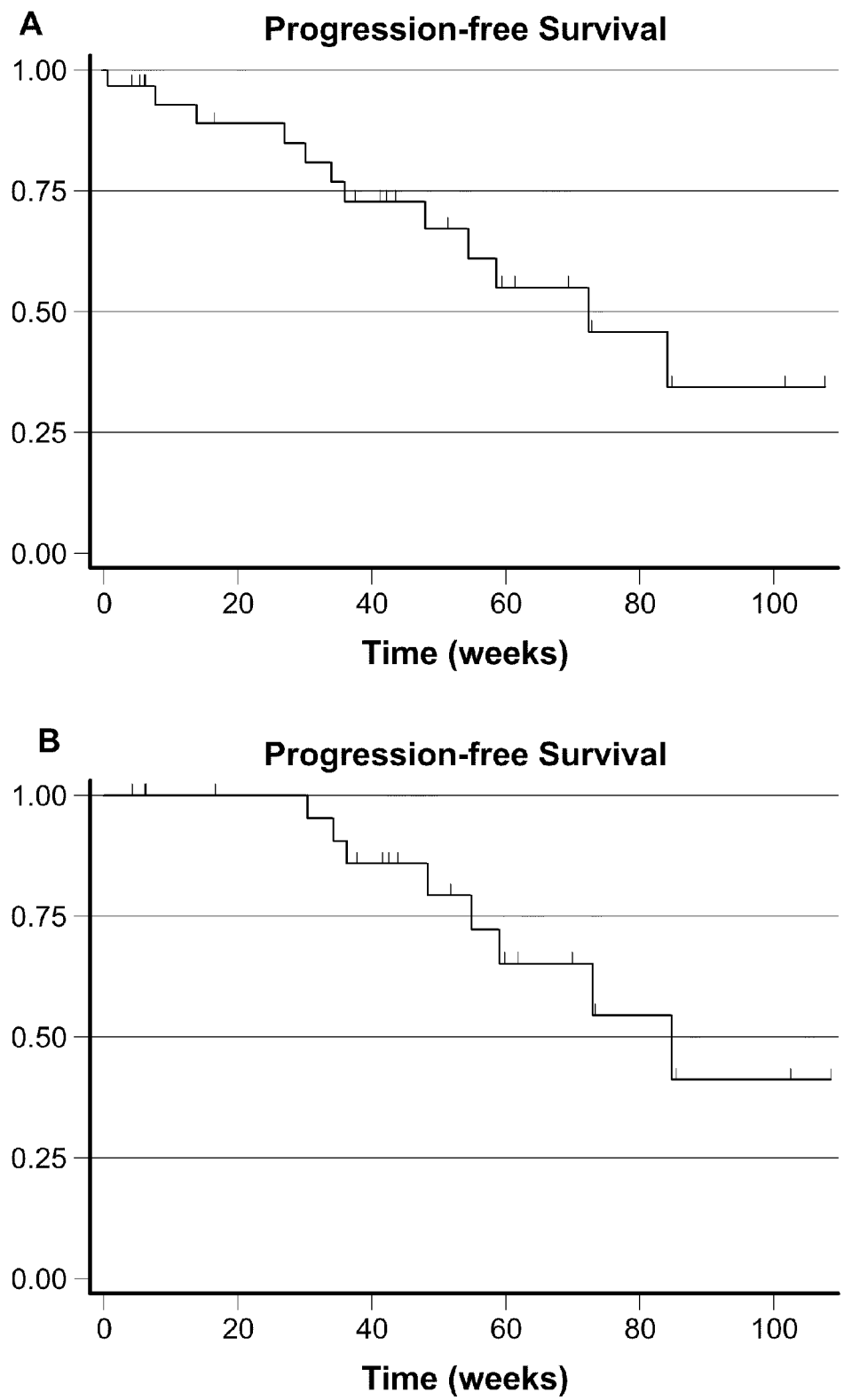
Figure 11:
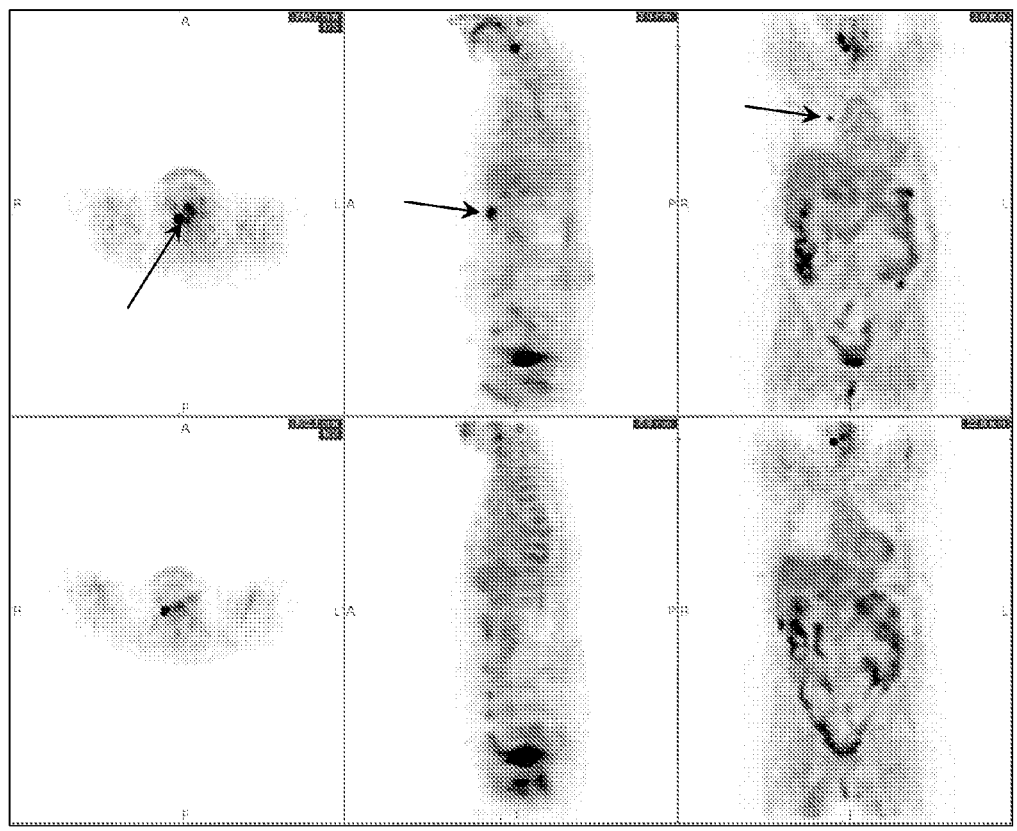

FIG. 10 shows that Kaplan Meier curves reveal a PFS of 72 weeks for all patients on study (A), and a PFS of 84 weeks for DTCs alone (B). Data reflect outcomes for the first 30 patients enrolled FIG. 11 shows FDG-PET uptake images at four weeks for detecting a response to sorafenib.

Figure 12:
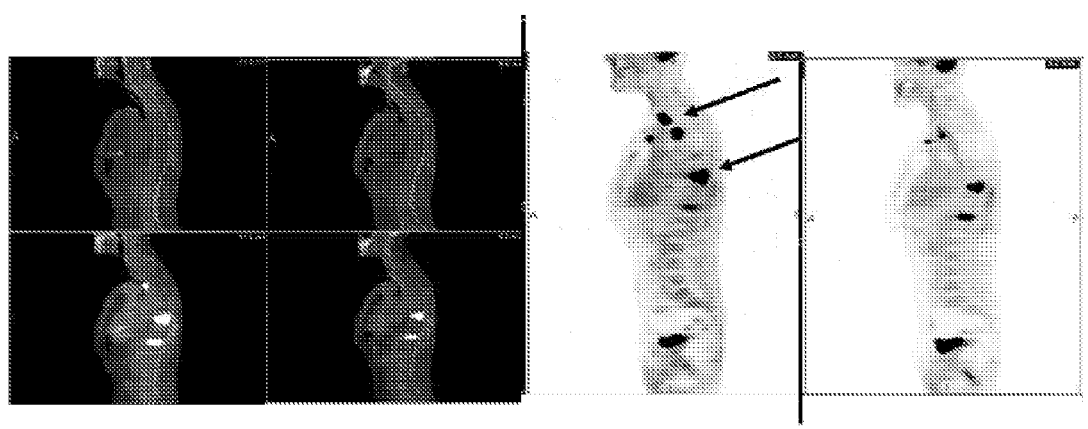

FIG. 12 shows FDG-PET uptake images at four weeks of treatment with sorafenib for detecting a response to sorafenib.

Figure 13:
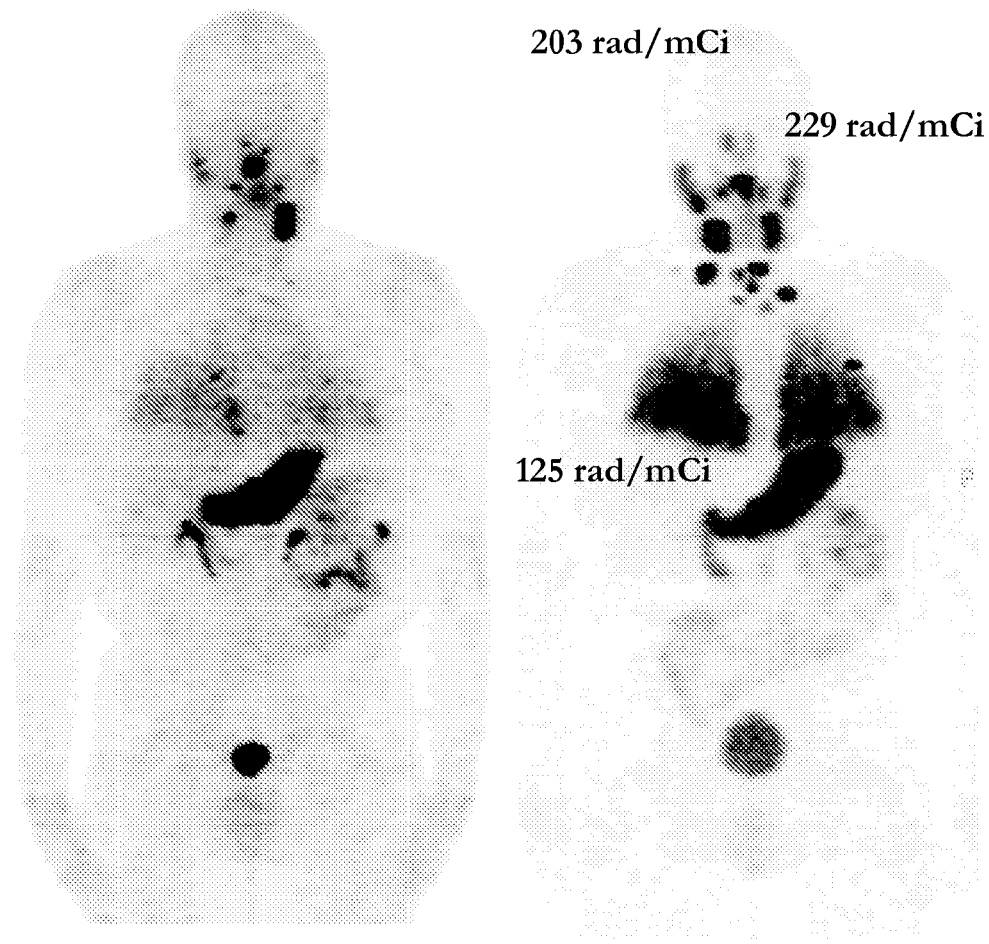

FIG. 13 shows $^{124}$I-Iodide PET detection in thyroid cancer.

Figure 14:
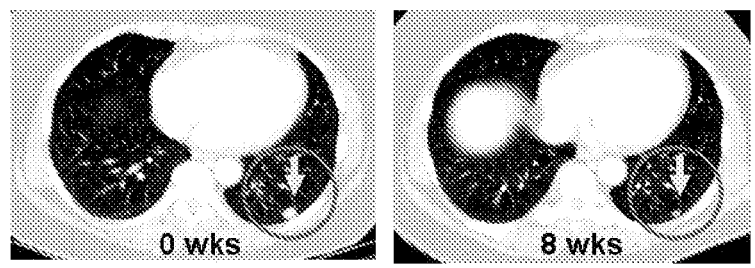
Figure 14:
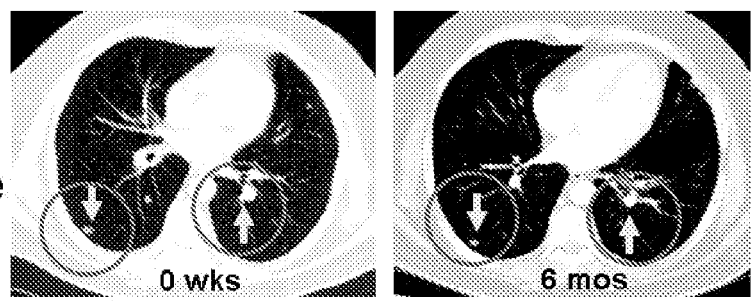

FIG. 14 shows CT images at 8 weeks and 6 months after the beginning of treatment with sorafenib.

Figure 15:
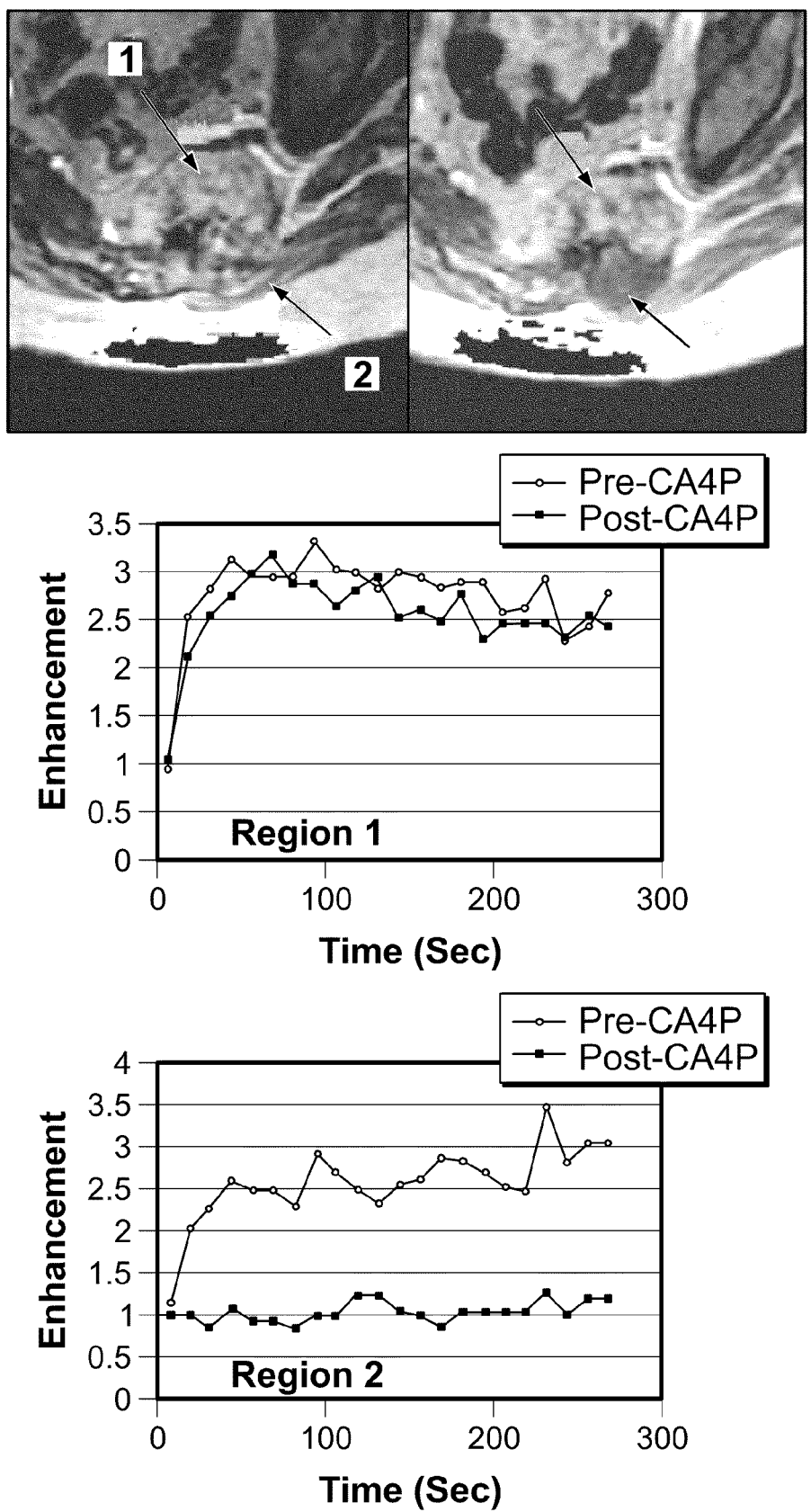

FIG. 15 shows heterogeneous response to therapy (CA4P) within a metastatic medullary thyroid.

DETAILED DESCRIPTION OF THE INVENTION

The invention relates to methods for treating thyroid cancer in a subject. Specifically, the invention relates to enhancing iodine absorption in thyroid by administering multi-kinase inhibitors, and thereby treating thyroid cancer.

In one embodiment, provided herein is a method for treating a thyroid cancer in a subject, comprising the step of enhancing iodine absorption in a thyroid in said subject by administering to said subject a composition comprising a multi-kinase inhibitor, thereby treating said thyroid cancer in said subject.

In another embodiment, provided herein is a method for treating a thyroid cancer in a subject, comprising the step of enhancing iodine absorption in a thyroid in said subject by administering to said subject a composition comprising sorafenib, thereby treating said thyroid cancer in said subject.

In another embodiment, provided herein is a method for enhancing iodine absorption in a thyroid in a subject, comprising the step of administering to said subject a composition comprising a multi-kinase inhibitor thereby enhancing iodine absorption in the thyroid in said subject.

In another embodiment, provided herein is a method for enhancing iodine absorption in a thyroid in a subject, comprising the step of administering to said subject a composition comprising sorafenib thereby enhancing iodine absorption in the thyroid in said subject.

In another embodiment, provided herein is a method for treating thyroid cancer in a subject before or after primary treatment, the method comprising administering to the subject in need of adjuvant or neoadjuvant therapy for thyroid cancer, a therapeutically effective amount of a composition comprising sorafenib.

In another embodiment, provided herein is a method for treating a thyroid cancer in a subject in need thereof, comprising the step of enhancing iodine absorption in a thyroid in said subject, wherein the step of enhancing iodine absorption comprises administering to said subject a composition comprising a multi-kinase inhibitor, thereby treating said thyroid cancer in said subject.

In another embodiment, provided herein is a method for providing a medical diagnosis based on radioactive iodine in a subject, comprising the step of administering to said subject a composition comprising a multi-kinase inhibitor, thereby providing said medical diagnosis in said subject.

In another embodiment, provided herein is a method for providing a medical diagnosis based on radioactive iodine in a subject, comprising the step of administering to said subject a composition comprising sorafenib, thereby providing said medical diagnosis in said subject.

In another embodiment, provided herein is a method for improving a medical diagnostic procedure based on radioactive iodine in a subject, comprising the step of administering to said subject a composition comprising a multi-kinase inhibitor, thereby improving said medical diagnostic procedure based on radioactive iodine in said subject.

In another embodiment, provided herein is a method for improving a medical diagnostic procedure based on radioactive iodine in a subject, comprising the step of administering to said subject a composition comprising sorafenib, thereby improving said medical diagnostic procedure based on radioactive iodine in said subject.

In another embodiment, provided herein is a medical diagnostic test comprising a radioactive iodine and a multi-kinase inhibitor.

In another embodiment, provided herein is a medical diagnostic test comprising a radioactive iodine and sorafenib.

In another embodiment, provided herein is a composition comprising an effective amount of a multi-kinase inhibitor for enhancing iodine absorption in a subject.

In another embodiment, provided herein is a composition comprising an effective amount of sorafenib for enhancing iodine absorption in a subject.

In another embodiment, provided herein is a composition comprising a multi-kinase inhibitor and iodine.

In another embodiment, provided herein is a composition comprising sorafenib and iodine.

In another embodiment, provided herein is a method for enhancing a radio labeled absorption in a bulky lymphoadenoma in a subject, comprising the step of administering to said subject a composition comprising a multi-kinase inhibitor thereby enhancing the radio labeled absorption in the lymphoadenoma in said subject.

In another embodiment, provided herein is a method for enhancing a radio labeled absorption in a bulky lymphoadenoma in a subject, comprising the step of administering to said subject a composition comprising sorafenib thereby enhancing the radio labeled absorption in the lymphoadenoma in said subject.

In another embodiment, provided herein is a method for treating a non radio labeled avid bulky Non-Hodgkin's Lymphoma in a subject, comprising the step of enhancing a non-radio labeled absorption in said bulky lymphoadenoma in said subject by administering to said subject a composition comprising a multi-kinase inhibitor, thereby treating said lymphoma in said subject.

In another embodiment, provided herein is a method for treating a non radio labeled-avid bulky Non-Hodgkin's Lymphoma in a subject, comprising the step of enhancing a non-radio labeled absorption in said bulky lymphoadenoma in said subject by administering to said subject a composition comprising sorafenib, thereby treating said bulky lymphoma in said subject.

In another embodiment, provided herein is a method for providing a medical diagnostic or therapeutic procedure for a bulky disease based on radioactive isotope in a subject, comprising the step of administering to said subject a composition comprising a multi-kinase inhibitor, thereby providing said medical diagnostic or therapeutic procedure in said subject.

In another embodiment, provided herein is a method for providing a medical diagnostic or therapeutic procedure for a bulky disease based on radioactive isotope in a subject, comprising the step of administering to said subject a composition comprising sorafenib, thereby providing said medical diagnostic or therapeutic procedure based on radioactive isotope in said subject.

In another embodiment, provided herein is a method for improving a medical diagnostic or therapeutic procedure for a bulky disease based on radioactive isotope in a subject, comprising the step of administering to said subject a composition comprising a multi-kinase inhibitor, thereby improving said medical diagnostic or therapeutic procedure based on radioactive isotope in said subject.

In another embodiment, provided herein is a method for improving a medical diagnostic or therapeutic procedure for a bulky disease based on radioactive isotope in a subject, comprising the step of administering to said subject a composition comprising sorafenib, thereby improving said medical diagnostic or therapeutic procedure based on radioactive isotope in said subject.

In another embodiment, provided herein is a composition comprising yttrium and sorafenib.

In another embodiment, provided herein is a method of providing prognosis for a thyroid cancer being treated with a multi-kinase inhibitor, comprising the step of simultaneously monitoring serum thyroglobulin (sTG), and tumor size, whereby a fall in sTG prior to change in tumor size indicates a positive treatment outcome using the multi-kinase inhibitor.

In one embodiment, the multi-kinase inhibitor is a small molecule multi-kinase inhibitor. In another embodiment, the multi-kinase inhibitor is sorafenib. In another embodiment, the multi-kinase inhibitor is sunitinib. In another embodiment, the multi-kinase inhibitor is imatinib (Gleevec). In another embodiment, the multi-kinase inhibitor is vandetinib. In another embodiment, the multi-kinase inhibitor is axitinib. In another embodiment, the multi-kinase inhibitor is motesanib (AMG-706).

In another embodiment, the multi-kinase inhibitor attacks the actual tumor and its ability to recruit new blood vessels essential for growth and dissemination via multiple mechanisms. In another embodiment, the multi-kinase inhibitor prevents cancer cell proliferation by inhibiting the RAF/MEK/ERK pathway and, in parallel, impedes angiogenesis by inhibiting vascular endothelial growth factor-2 (VEGF-2) and platelet-derived growth factor-beta (PDGF-β). In another embodiment, the multi-kinase inhibitor targets other kinases including FLT-3 and c-KIT. In another embodiment, the multi-kinase inhibitor targets VEGF and PDGF-α and β as well as FLT-3 and c-KIT. In another embodiment, the multi-kinase inhibitor inhibits BRAF signaling. In another embodiment, the inhibitor up-regulates iodine-metabolizing genes.

In another embodiment, the multi-kinase inhibitor inhibits tumor growth in a patient afflicted with a thyroid tumor. In another embodiment, the multi-kinase inhibitor inhibits tumor growth in a patient afflicted with metastatic differentiated thyroid cancer. In another embodiment, the multi-kinase inhibitor inhibits tumor growth in a patient afflicted with metastatic differentiated thyroid cancer not amenable to radioiodine therapy. In another embodiment, the multi-kinase inhibitor treats an iodine non-avid disease. In another embodiment, the multi-kinase inhibitor is used together with iodine. In another embodiment, the multi-kinase inhibitor is used in case of accidents that could lead to releases of radioactive iodine. In another embodiment, the multi-kinase inhibitor is used to treat patients afflicted with iodine deficiency. In another embodiment, the multi-kinase inhibitor is used together with iodine to treat patients afflicted with iodine deficiency. In another embodiment, the multi-kinase inhibitor is used together with iodine to treat patients afflicted with a thyroid cancer.

In another embodiment, the multi-kinase inhibitor enhances iodine absorption in a thyroid in a patient afflicted with a thyroid tumor. In another embodiment, the multi-kinase inhibitor enhances iodine absorption in a thyroid in a patient afflicted with metastatic differentiated thyroid cancer. In another embodiment, the multi-kinase inhibitor enhances iodine absorption in a thyroid in a patient afflicted with a metastatic differentiated thyroid cancer not amenable to radioiodine therapy.

In another embodiment, a method comprising the use of a multi-kinase inhibitor enables the use of reduced amounts of radioactive iodine. In another embodiment, a method comprising the use of a multi-kinase inhibitor for treating thyroid cancer enables the use of reduced amounts of radioactive iodine.

In another embodiment, methods utilizing a multi-kinase inhibitor are effective for a period of up to 20 months of continuous treatment. In another embodiment, methods utilizing a multi-kinase inhibitor for enhancing iodine absorption are effective for a period of up to 20 months of continuous treatment. In another embodiment, methods utilizing a multi-kinase inhibitor for enhancing iodine absorption in a differentiated thyroid cancer are effective for a period of up to 20 months of continuous treatment.

In another embodiment, methods utilizing a multi-kinase inhibitor are effective for a period of up to 17 months of continuous treatment. In another embodiment, methods utilizing a multi-kinase inhibitor for enhancing iodine absorption are effective for a period of up to 17 months of continuous treatment. In another embodiment, methods utilizing a multi-kinase inhibitor for enhancing iodine absorption in a differentiated thyroid cancer are effective for a period of up to 17 months of continuous treatment.

In another embodiment, methods utilizing sorafenib are effective for a period of up to 20 months of continuous treatment. In another embodiment, methods utilizing sorafenib for enhancing iodine absorption are effective for a period of up to 20 months of continuous treatment. In another embodiment, methods utilizing sorafenib for enhancing iodine absorption in a differentiated thyroid cancer are effective for a period of up to 20 months of continuous treatment.

In another embodiment, methods utilizing sorafenib are effective for a period of up to 17 months of continuous treatment. In another embodiment, methods utilizing sorafenib for enhancing iodine absorption are effective for a period of up to 17 months of continuous treatment. In another embodiment, methods utilizing sorafenib for enhancing iodine absorption in a differentiated thyroid cancer are effective for a period of up to 17 months of continuous treatment.

In another embodiment, a multi-kinase inhibitor reverses the differentiation process of a cell in a thyroid cell and enhances the cell's ability to absorb iodine. In another embodiment, a multi-kinase inhibitor enhances absorption of iodine by thyroid cancer cells by at least 10%. In another embodiment, a multi-kinase inhibitor enhances absorption of iodine by thyroid cancer cells by at least 20%. In another embodiment, a multi-kinase inhibitor enhances absorption of iodine by thyroid cancer cells by at least 30%. In another embodiment, a multi-kinase inhibitor enhances absorption of iodine by thyroid cancer cells by at least 40%. In another embodiment, a multi-kinase inhibitor enhances absorption of iodine by thyroid cancer cells by at least 60%. In another embodiment, a multi-kinase inhibitor enhances absorption of iodine by thyroid cancer cells by at least 80%. In another embodiment, a multi-kinase inhibitor enhances absorption of iodine by thyroid cancer cells by at least 100%. In another embodiment, a multi-kinase inhibitor enhances absorption of iodine by thyroid cancer cells by at least 2 folds. In another embodiment, a multi-kinase inhibitor enhances absorption of iodine by thyroid cancer cells by at least 4 folds. In another embodiment, a multi-kinase inhibitor enhances absorption of iodine by thyroid cancer cells by at least 8 folds. In another embodiment, a multi-kinase inhibitor enhances absorption of iodine by thyroid cancer cells by at least 10 folds. In another embodiment, a multi-kinase inhibitor enhances absorption of iodine by thyroid cancer cells by at least 15 folds.

In another embodiment, iodine is a radioactive iodine. In another embodiment, radioiodine is an isotope with a shorter half-live. In another embodiment, the radioiodine is $^{131}$I. In another embodiment, the radioiodine is $^{123}$I. In another embodiment, the radioiodine is $^{125}$I. In another embodiment, the radioiodine is $^{129}$I. In another embodiment, iodine is an iodide of sodium or potassium. In another embodiment, iodine is an iodate.

In another embodiment, a multi-kinase inhibitor is administered concomitantly with iodine. In another embodiment, a multi-kinase inhibitor is administered concomitantly with radioactive iodine. In another embodiment, a multi-kinase inhibitor is administered in a single composition with radioactive iodine. In another embodiment, a multi-kinase inhibitor In one embodiment, the multi-kinase inhibitors described herein, are used in combination with other anti-cancer agents, In another embodiment, the multi-kinase inhibitor is administered to a patient afflicted with thyroid cancer in combination with Adriamycin. In another embodiment, the multi-kinase inhibitor is administered to a patient afflicted with thyroid cancer prior to treatment with Adriamycin. In another embodiment, the multi-kinase inhibitor is administered to a patient afflicted with thyroid cancer after treatment with Adriamycin. In one embodiment, the anti-cancer agent used in combination with the multi-kinase inhibitors described herein is axitinib, or in another embodiment, cisplatin, bleomycin, vinblastine, methotrexate, or their combinations in other discrete embodiments. In another embodiment, the multi-kinase inhibitor is administered in combination with adriamycine, axtinib, cisplatin, bleomycin, vinblastine, methotrexate, or their combination; and another agent (i.e., three agent combination), such as cyclophosphamide in one embodiment, or vinscristine, dacarbazine, etoposide, peplomycin, paclitaxel, epirubicin, or their combination. A person skilled in the art would readily recognize that the combination agents described herein, could be given before, after or during the course of radiotherapy as described herein.

In one embodiment, the, the anti-cancer agent used in combination with the multi-kinase inhibitors described herein, such as sorafenib in one embodiment, is a radioactive isotope emitting sub-atomic particles that induce tumor death in the irradiated tumor, or for diagnostic purposes in other discrete embodiments. These isotopes are in one embodiment $^{137}$Cesium, $^{60}$Cobalt or their combination. $^{137}$Cesium is used in one embodiment in LDR treatment of gynecologic cancers. In another embodiment, a specialized housing comprising the radioactive source is used in another embodiment. Optimal placement of the uterine and vaginal housing produces in one embodiment, a radioative distribution that delivers a high dose to the cervix and paracervical tissues while simultaneously reducing the dose to the rectum and bladder. In one embodiment, the multi-kinase inhibitors described herein are administered to the target tissue to increase the efficiency of the radiation, thereby allowing for a lower dose of radiation. In another embodiment, $^{131}$Cesium seeds are implanted in an organ of the subject and are subjected to teletherapy using $^{60}$Cobalt source. In another embodiment, the multi-kinase inhibitors described herein, such as sorafenib in one embodiment, is administered to the organ or tissue of the subject, in conjunction with the seed implantation of the radioisotopes described herein.

In another embodiment, the radioisotope is $^{137}$Cesium, or $^{131}$Cesium, $^{125}$I, $^{103}$Pd, $^{142}$Pr, $^{185-196}$Au, $^{198-201}$Au, $^{203}$Au or their combination in other discrete embodiments of the use of combination brachytherapy using the multi-kinase inhibitors described herein, such as sorafenib in one embodiment.

In one embodiment, compositions comprising the multi-kinase inhibitors described herein, such as sorafenib in one embodiment described herein are also used in combination with diagnostic radioisotopes, such as $^{153}$Gd in one embodiment, or $^{3}$H, $^{13}$C, $^{32}$P, Deutirium or their combination in other discrete embodiments.

In another embodiment, a combination therapy comprises administering at least one multi-kinase inhibitor. In another embodiment, a combination therapy comprises administering a combination of multi-kinase inhibitors. In another embodiment, a combination therapy comprises administering at least one multi-kinase inhibitor and a chemotherapeutic agent. In another embodiment, a combination therapy comprises radiotherapy and administration of at least one multi-kinase inhibitor. In another embodiment, a combination therapy comprises radiotherapy and administration of at least one multi-kinase inhibitor and radioactive iodine.

In one embodiment, the compositions used in the methods described herein, comprises an additional agent in combination with sorafenib (Nexavar™). In another embodiment, the additional compounds used in the compositions and methods described herein, is a substituted diphenyl, quinolyl, isoquinolyl, pyridyl urea or their combination. In another embodiment, the multi-kinase inhibitor used is a substituted diphenyl, quinolyl, isoquinolyl, pyridyl urea or their combination. In one embodiment, the iodine used in the methods described herein is Sodium iodide $^{131}$I (DraxImage™) a radioactive iodine approved for use in evaluating thyroid function and for localization of cancer that has metastasized outside the thyroid. In another embodiment, other multikinase inhibitors that interfere with multiple kinase enzymes used by tumor cells to grow and multiply, are used in addition to sorafenib in the methods described herein.

In one embodiment, the additional multikinase inhibitors used in addition to sorafenib is Sunitinib (Sutent™, Pfizer). In one embodiment, the additional agent used in addition to sorafenib is Tanespimycin (KOS-953 or 17-AAG), which is ageldanamycin analog that binds to heat-shock protein 90 (HSP90). In another embodiment, binding to HSP90 results in the downregulation of a number of proteins, including tyrosine kinases in one embodiment, or transcription factors in another, thereby causing cancer cell death. In one embodiment, the additional agent used in addition to sorafenib is bortezomib (Velcade™, Millennium), a proteosome inhibitor. In one embodiment, the additional agent used in addition to sorafenib is Vandetanib (Zactima™, AstraZeneca a.k.a ZD6474), which inhibits tumor vascular growth and tumor cell proliferation. In one embodiment, the additional agent used in addition to sorafenib is Romidepsin (Gloucester), which is a histone deacetylase inhibitor (a.k.a. FK228, FR901228, and depsipeptide). In one embodiment romidepsin causes tumor cell death and exhibits antitumor activity. Another tyrosine kinase inhibitor used in conjunction with sorefanib in the methods and compositions described herein, is gefitinib (Iressa™, AstraZeneca), which exhibits antitumor effects in thyroid cancer. In one embodiment, the additional agent used in addition to sorafenib is irinotecan (Camptosar™, Pfizer) or AG-013736 in another embodiment. Irinotecan binds in one embodiment to topoisomerase I and causes cancer cell death. AG-013736 refers in another embodiment to an additional a tyrosine kinase inhibitor. In one embodiment, the additional agent used in addition to sorafenib is lenalidomide (Revlimid™, Celgene) in one embodiment, or rosiglitazone (Avandia™, GlaxoSmithKline) in another embodiment. Lenalidomide refers in one embodiment to thalidomide analog either by itself or in combination with dexamethasone in another embodiment. Rosiglitazone refers in another embodiment to a drug that increases thyroid tumor cell sensitivity to iodine. In one embodiment, the additional agent used in addition to sorafenib is Belinostat (PXD101) or belinostat/5-fluorouracil combination in another embodiment.

In another embodiment, the composition comprises a multi-kinase inhibitor. In another embodiment, the composition comprises a multi-kinase inhibitor and an iodine source. In another embodiment, the composition comprises a multi-kinase inhibitor and a radioactive iodine. In another embodiment, the composition comprises a multi-kinase inhibitor and rosiglitazone. In another embodiment, the composition comprises a multi-kinase inhibitor, rosiglitazone, and an iodine source.

In another embodiment, the composition comprises a multi-kinase inhibitor and Cabretastatin. In another embodiment, the composition comprises a multi-kinase inhibitor, Cabretastatin, and an iodine source.

In another embodiment, the composition comprises a multi-kinase inhibitor and Lenalidomide. In another embodiment, the composition comprises a multi-kinase inhibitor, Lenalidomide, and an iodine source.

In another embodiment, the composition comprises a multi-kinase inhibitor and 17-AAG. In another embodiment, the composition comprises a multi-kinase inhibitor, 17-AAG, and an iodine source. In another embodiment, the composition comprises a multi-kinase inhibitor and 17-DMAG. In another embodiment, the composition comprises a multi-kinase inhibitor, 17-DMAG, and an iodine source.

In another embodiment, the composition comprises a multi-kinase inhibitor and Depsipeptide (FR901228). In another embodiment, the composition comprises a multi-kinase inhibitor, Depsipeptide, and an iodine source.

In another embodiment, the composition comprises a multi-kinase inhibitor and Decitabine. In another embodiment, the composition comprises a multi-kinase inhibitor, Decitabine, and an iodine source.

In another embodiment, the composition comprises a multi-kinase inhibitor and Bortezomib. In another embodiment, the composition comprises a multi-kinase inhibitor, Bortezomib, and an iodine source.

In another embodiment, the composition comprises a multi-kinase inhibitor and Irinotecan. In another embodiment, the composition comprises a multi-kinase inhibitor, Irinotecan, and an iodine source.

In one embodiment, the composition comprises a multi-kinase inhibitor, such as sorafenib and a MET inhibitor, a mTOR inhibitor or their combination. In one embodiment, the MET inhibitor is a multi-kinase inhibitor, a competitive inhibitor, a nucleic acid, an antibody, an antibody fragment, or an aptamer. In one embodiment, the Met inhibitor is PHA-665752 ((3Z)-5-[(2,6-dichlorobenzyl)sulfonyl]-3-[(3,5-dimethyl-4-{[(2R)-2-(pyrrol-idin-1-ylmethyl)pyrrolidin-1-yl]carbonyl}-1H-pyrrol-2-yl)methylene]-1,3-di-hydro-2H-indol-2-one), PF-02341066. Embodiments of c-met inhibitor antibodies include c-met inhibitors that interfere with binding of a ligand such as HGF to c-met. In one embodiment, a c-met inhibitor may bind to c-met such that binding of HGF to c-met is inhibited. In one embodiment, an antagonist antibody is a chimeric antibody, in one embodiment, an antibody comprising antigen binding sequences from a non-human donor grafted to a heterologous non-human, human or humanized sequence (e.g., framework and/or constant domain sequences). In one embodiment, the non-human donor is a mouse. In one embodiment, an antigen binding sequence is synthetic, e.g. obtained by mutagenesis (e.g., phage display screening, etc).

In one embodiment, mTOR is an important signaling intermediate molecule downstream of the PI3K/AKT pathway that inhibits apoptosis, and is important in nutritional status checkpoint. mTOR is a large ($M_W$ 289,000) multidomain serine/threonine kinase, and is a member of the PI3K family of protein kinases based on homology within its catalytic domain. In another embodiment, Mammalian target of rapamycin ("mTOR") regulates the activity of at least two proteins involved in the translation of specific cell cycle regulatory proteins. One of these proteins, p70s6 kinase, is phosphorylated by mTOR on serine 389 as well as threonine 412. This phosphorylation is observed in growth factor treated cells in another embodiment, by Western blotting of whole cell extracts of these cells with antibody specific for the phosphoserine 389 residue. As used herein, the term "mTOR inhibitor" refers in one embodiment to a compound or ligand which inhibits cell replication by blocking progression of the cell cycle from G1 to S by inhibiting the phosphorylation of serine 389 of p70s6 kinase by mTOR. One skilled in the art can readily determine if a compound, such as a rapamycin derivative, is an mTOR inhibitor.

In another embodiment, mTOR inhibitors used in conjunction with the multi-kinase inhibitors provided herein (e.g. Sorafenib in one embodiment), is everolimus, a 4-O-(2-hydroxyethyl)-rapamycin derived from a macrolide antibiotic produced by *Streptomyces hygroscopicus*, also known as Certican, RAD-001 and SDZ-RAD. In one embodiment, the mTOR inhibitor is tacrolimus, a macrolide lactone immunosuppressant isolated from the soil fungus *Streptomyces tsukubaensis*, also known as FK 506, FR 900506, Fujimycin, L 679934, Tsukubaenolide, Protopic and Prograf. In another embodiment, the mTOR inhibitor is ABT-578 an antiproliferative agent, AP-23675, AP-23573, or AP-23841 and their combination in other embodiments.

In one embodiment, in cases of non-$^{131}$I-avid tumors, as demonstrated by negative $^{131}$I whole body scan, ocular external beam radiation remains a therapeutic option. In another embodiment, metastatic well differentiated thyroid cancer (WTC) to the bone demonstrates a poor response to $^{131}$I treatment. Accordingly, in one embodiment, patients undergoing external beam radiation for hurthle cell carcinoma in one embodiment, or bone cancer resulting from metastatic thyroid cancer, are administered a composition comprising $^{131}$I and sorafenib, according to the regimens described hereinbelow. In another embodiment, the compositions of the invention, comprise $^{131}$I and sorafenib, for the use in the treatment of tumors using external beam radiation.

In another embodiment, sorafenib is further used in combination with other chemotherapeutic agents to increase their efficacy in treating thyroid cancer. In another embodiment, sorafenib is further used in combination with other chemotherapeutic agents to increase their efficacy in treating a metastatic thyroid cancer. In another embodiment, sorafenib is used in combination with other kinase inhibitors. In another embodiment, sorafenib is used in combination with an anti-angiogenic agent. In another embodiment, sorafenib is used in combination with HSP90 inhibitor. In another embodiment, sorafenib is used in combination with Histone deacetylase inhibitor. In another embodiment, sorafenib is used in combination with a proteasome inhibitor. In another embodiment, sorafenib enhances the effectiveness of chemotherapeutic agents. In another embodiment, sorafenib and a chemotherapeutic agent have a synergistic effect in treating cancer. In another embodiment, sorafenib and a chemotherapeutic agent have a synergistic effect in treating thyroid cancer.

In another embodiment, a multi-kinase inhibitor, for example, sorafenib is used in combination with an agent that inhibits VEGF-2, PDGF-α, PDGF-β, FLT-3, or c-KIT. In some embodiments, the agent comprises Bevacizumab, Imatinib (STI157), Leflunomide (SU101), Midostaurin (PKC412), Semaxanib (SU5416), Vatalanib (PTK787), Recentin (AZD2171), AG013736, AZD2171, CDP860, CP547,632, CP673,451, RPI 4610, SU6668, VEGF-trap, ZD6474, YM359445, or combinations thereof. In another embodiment, a multi-kinase inhibitor, for example, sorafenib is used in combination with an agent inhibits the RAF/MEK/ERK pathway. Examples of an agent inhibiting the RAF/MEK/ERK pathway include, but are not limited to, Bay 43-9006, CI-1040, ISIS 5132, or combinations thereof.

In another embodiment, the composition comprises 20-1000 mg of a multi-kinase inhibitor. In another embodiment, the composition comprises 20-100 mg of a multi-kinase inhibitor. In another embodiment, the composition comprises 20-50 mg of a multi-kinase inhibitor. In another embodiment, the composition comprises 50-100 mg of a multi-kinase inhibitor. In another embodiment, the composition comprises 50-200 mg of a multi-kinase inhibitor. In another embodiment, the composition comprises 100-300 mg of a multi-kinase inhibitor. In another embodiment, the composition comprises 200-400 mg of a multi-kinase inhibitor. In another embodiment, the composition comprises 300-500 mg of a multi-kinase inhibitor. In another embodiment, the composition comprises 400-600 mg of a multi-kinase inhibitor. In another embodiment, the composition comprises 500-700 mg of a multi-kinase inhibitor. In another embodiment, the composition comprises 700-1000 mg of a multi-kinase inhibitor.

In another embodiment, the composition comprises 20-1000 mg sorafenib. In another embodiment, the composition comprises 20-100 mg sorafenib. In another embodiment, the composition comprises 20-50 mg sorafenib. In another embodiment, the composition comprises 50-100 mg sorafenib. In another embodiment, the composition comprises 50-200 mg sorafenib. In another embodiment, the composition comprises 100-300 mg sorafenib. In another embodiment, the composition comprises 200-400 mg sorafenib. In another embodiment, the composition comprises 300-500 mg sorafenib. In another embodiment, the composition comprises 400-600 mg sorafenib. In another embodiment, the composition comprises 500-700 mg sorafenib. In another embodiment, the composition comprises 700-1000 mg sorafenib.

In another embodiment, the invention provides a method of treating a thyroid cancer in a subject, comprising the step of enhancing iodine absorption in a thyroid in said subject by administering to said subject a composition comprising a multi-kinase inhibitor, thereby treating said thyroid cancer in said subject. In another embodiment, the invention provides a method of treating a thyroid cancer in a subject, comprising the step of enhancing iodine absorption in a thyroid in said subject by administering to said subject a composition comprising sorafenib, thereby treating said thyroid cancer in said subject.

In another embodiment, the invention provides a method of enhancing iodine absorption in a thyroid in a subject, comprising the step of administering to said subject a composition comprising a multi-kinase inhibitor, thereby enhancing iodine absorption in the thyroid in said subject. In another embodiment, the invention provides a method of enhancing iodine absorption in a thyroid in a subject, comprising the step of administering to said subject a composition comprising sorafenib, thereby enhancing iodine absorption in the thyroid in said subject.

The terms "treat", "treating" and "treatment", as used herein, refer to ameliorating symptoms associated with a disease or condition, for example, a thyroid cancer, including preventing or delaying the onset of the disease symptoms, and/or lessening the severity or frequency of symptoms of the disease or condition. The terms "subject" and "individual" are defined herein to include animals, such as mammals, including but not limited to, primates, cows, sheep, goats, horses, dogs, cats, rabbits, guinea pigs, rats, mice or other bovine, ovine, equine, canine, feline, rodent, or murine species. In a preferred embodiment, the mammal is a human. In one embodiment, the subject is a human patient who failed to respond to a prior standard care cancer treatment. In another embodiment, the subject is a human patient who was diagnosed with a risk of unsuccessful outcome for a cancer treatment.

As used herein, an "effective amount" of a therapeutic compound is an amount sufficient to inhibit proliferation of a cancer cell in a subject suffering from a cancer. One skilled in the art can readily determine an effective amount of a therapeutic compound to be administered to a given subject, by taking into account factors, such as the size and weight of the subject; the extent of disease penetration; the age, health and sex of the subject; the route of administration; and whether the administration is regional or systemic.

In another embodiment, the cancer diagnosed or treated by the invention is a thyroid cancer. In another embodiment, the thyroid cancer is a differentiated thyroid cancer. In another embodiment, the differentiated thyroid cancer is a follicular differentiated thyroid cancer. In another embodiment, the differentiated thyroid cancer is a papillary differentiated thyroid cancer. In another embodiment, the thyroid cancer is a benign thyroid cancer. In another embodiment, the thyroid cancer is a metastatic thyroid cancer. In another embodiment, the thyroid cancer is a remote metastatic thyroid cancer. In one embodiment, the thyroid cancer is Hurthle Cell carcinoma, or in another embodiment, medullary thyroid cancer or anaplastic thyroid cancer in another embodiment. In one particular embodiment, the thyroid cancer is a caner that lost ability to absorb iodine. In another particular embodiment, the thyroid cancer is an iodine non avid or iodine refractory thyroid cancer. In another particular embodiment, the thyroid cancer is an iodine non avid metastatic thyroid cancer.

In another embodiment, a thyroid cancer comprises a papillary tumor. In another embodiment, a thyroid cancer comprises a follicular tumor. In another embodiment, a thyroid cancer comprises a medullary tumor. In another embodiment, a thyroid cancer comprises an anaplastic tumor. In one embodiment thyroid cancer is Hurthle Cell carcinoma. Hürthle cell thyroid cancer refers to an uncommon and occasionally aggressive differentiated thyroid malignancy particularly when the primary tumor is widely invasive. In one embodiment, Hürthle cell thyroid cancer has a higher incidence of distant metastasis (33%) than other differentiated thyroid cancers (range, 10%-22% in papillary or follicular thyroid cancers). In another embodiment, The combination of serum thyroglobulin (Tg) measurements and radioiodine scintigraphy (RIS) is used for the detection of residual or metastatic disease. In one embodiment, Hürthle cell thyroid cancer has generally low iodine avidity. In another embodiment, medical re-differentiation therapies to increase iodine avidity have had generally disappointing results. Accordingly, using sorafenib according to the methods described herein, increases the iodine avidity in Hurthle cell carcinoma.

In another embodiment, the thyroid cancer is a conventional type follicular carcinoma. In another embodiment, the thyroid cancer is an oncocytic variant of follicular carcinoma. In another embodiment, the thyroid cancer is a follicular adenoma. In another embodiment, the thyroid cancer is a conventional type follicular adenoma. In another embodiment, the thyroid cancer is an oncocytic variant of follicular adenoma.

In another embodiment, the cancer is an early stage thyroid cancer. In another embodiment, the cancer is an advanced thyroid cancer. The terms "advanced thyroid cancer," as used herein, refer to a thyroid cancer that has not been cured by local measures including surgery and external beam radiation, and is not amenable to additional radio active iodine therapy. In another embodiment, the cancer is a stage I thyroid cancer. In another embodiment, the cancer is a stage II thyroid cancer. In another embodiment, the cancer is a stage III thyroid cancer.

In another embodiment, the cancer occurs in follicular cells. In another embodiment, the cancer occurs in para follicular cells. In another embodiment, the cancer occurs in lymphocytes. In another embodiment, the cancer occurs in stromal cells. In another embodiment, the cancer occurs in thyroid lobe cells. In another embodiment, the cancer occurs in hurthle cells.

In a particular embodiment, the cancer diagnosed or treated by the invention is a cancer that is mediated by the BRAF gene. Examples of BRAF mediated cancer include, but are not limited to, melanoma, colorectal cancer, gastric cancer, endometrial cancer, thyroid cancer, lung cancer, adenocarcinoma, and lymphoma.

In another embodiment, the cancer that may be diagnosed or treated by the invention include tumors that are not vascularized, or not yet substantially vascularized, as well as vascularized tumors. The cancers may be comprised of non-solid tumors (such as leukemias and lymphomas) or may be solid tumors.

Cancers diagnosed or treated by the invention may also include carcinoma, blastoma, and sarcoma, and certain leukemia or lymphoid malignancies, benign and malignant tumors, and malignancies e.g., sarcomas, carcinomas, and melanomas. Adult tumors/cancers and pediatric tumors/cancers alike may be treated in accordance with the invention.

In another embodiment, a multi-kinase inhibitor is administered to a patient afflicted with metastatic thyroid cancer. In another embodiment, a multi-kinase inhibitor is administered to a patient afflicted with metastatic thyroid cancer that lost the ability to take up iodine. In another embodiment, iodine uptake inversely correlates with survival. In another embodiment, a multi-kinase inhibitor increases the survival of a patient afflicted with metastatic thyroid cancer.

In another embodiment, a multi-kinase inhibitor induces early reduction in tumor volume. In another embodiment, a multi-kinase inhibitor comprising anti-vascular activity induces early reduction in tumor volume. In another embodiment, a multi-kinase inhibitor comprising anti-vascular activity induces early reduction in tumor volume mediated through the inhibition of the mitogenic Receptor Tyrosine Kinase (RTK) RAS-RAF-MEK-ERK pathway on cellular differentiation.

In another embodiment, a multi-kinase inhibitor induces cell differentiation. In another embodiment, a multi-kinase inhibitor induces cancerous cell differentiation. In another embodiment, a multi-kinase inhibitor induces thyroid cell differentiation. In another embodiment, a multi-kinase inhibitor induces thyroid cancer cell differentiation.

In another embodiment, a multi-kinase inhibitor induces iodine metabolism. In another embodiment, a multi-kinase inhibitor induces iodine metabolism in a cancerous cell. In another embodiment, a multi-kinase inhibitor induces iodine metabolism in a thyroid cell. In another embodiment, a multi-kinase inhibitor induces iodine metabolism in a thyroid cancer cell.

In another embodiment, a multi-kinase inhibitor induces the activity of the sodium iodide symporter (NIS). In another embodiment, a multi-kinase inhibitor induces the expression of NIS. In another embodiment, a multi-kinase inhibitor induces NIS in a cancerous cell. In another embodiment, a multi-kinase inhibitor induces NIS in a thyroid cell. In another embodiment, a multi-kinase inhibitor induces NIS in a thyroid cancer cell.

In another embodiment, a multi-kinase inhibitor restores the expression of the iodine metabolizing genes in thyroid cells. In another embodiment, a multi-kinase inhibitor restores the expression of the iodine metabolizing genes in thyroid cancer cells. In another embodiment, a multi-kinase inhibitor induces the expression of TSHr, NIS, TG, Pax-8, or any combination thereof in a thyroid cell. In another embodiment, a multi-kinase inhibitor restores the expression of TSHr, NIS, TG, Pax-8, or any combination thereof in a thyroid cancer cell. In another embodiment, a multi-kinase inhibitor inhibits RAF, and restores iodine uptake. In another embodiment, a multi-kinase inhibitor inhibits RAF, and enhances iodine uptake in a thyroid cancer cell. In another embodiment, a multi-kinase inhibitor inhibits RAF, and enhances iodine uptake in a thyroid cell.

In another embodiment, a multi-kinase inhibitor treats thyroid cancer characterized by the expression of $BRAF^{V600E}$.

In another embodiment, a multi-kinase inhibitor which is sorafenib is effective in treating a patient afflicted with differentiated thyroid carcinoma (DTC) (see experimental section). In another embodiment, sorafenib has an initial cytoreduction phase in the first two to six months, followed by a static phase where tumor lesions no longer change in size, but increase secretion of sTG. In another embodiment, sorafenib inhibits angiogenesis. In another embodiment, sorafenib leads to reduced PI3K and MAPK signaling at early time points in treatment, and with decreases in the EC being more pronounced than those in the TC. In another embodiment, Ki-67 expression is quite low in the pre-treatment period (FIGS. 11 and 12). In another embodiment, this effect is anti-vascular. In another embodiment, sTG begins to rise quickly, and may rise in the absence of increased tumor burden. In another embodiment, the uncoupling of the tumor burden with sTG is suggestive that re-expression of iodine metabolizing genes are occurring, mirroring observations made in response to changes in RAF-MEK-ERK signaling observed in vivo and in vitro.

In another embodiment, the invention provides a method of treating thyroid cancer in a subject before or after primary treatment, the method comprising administering to a subject in need of adjuvant or neoadjuvant therapy for thyroid cancer, a therapeutically effective amount of a composition comprising a multi-kinase inhibitor. In another embodiment, the invention provides a method of treating thyroid cancer in a subject before or after primary treatment, the method comprising administering to a subject in need of adjuvant or neoadjuvant therapy for thyroid cancer, a therapeutically effective amount of a composition comprising sorafenib.

In one embodiment, the primary treatment comprises a radioactive iodine therapy. In another embodiment, the primary treatment comprises a surgery. In one embodiment, the compositions described herein are administered to the subject before ablation of postsurgical foci, or in another embodiment, after surgery.

In another embodiment, a multi-kinase inhibitor is used prior to a surgical procedure comprising removal of a cancerous tissue. In another embodiment, a multi-kinase inhibitor is used prior to a surgical procedure comprising removal of a cancerous thyroid tissue. In another embodiment, a multi-kinase inhibitor enhances the efficacy of a surgical procedure by reducing the tumor size. In another embodiment, a multi-kinase inhibitor enhances the efficacy of a surgical procedure, in a cancerous thyroid, by reducing the tumor size. In another embodiment, a multi-kinase inhibitor is administered to a patient afflicted with thyroid cancer prior to surgery and radioactive iodine is administered to a patient after surgery. In another embodiment, a patient undergoes thyroidectomy followed by RAI ($^{131}$I) ablation. In another embodiment, the patient further undergoes TSH suppression therapy with thyroid hormone.

In another embodiment, a multi-kinase inhibitor is administered to a patient afflicted with thyroid cancer prior to surgery in order to sensitize post-surgery, remnant, cancerous cells to radioactive iodine. In another embodiment, a multi-kinase inhibitor is administered to a patient afflicted with thyroid cancer prior to surgery in order induce iodine metabolism in post-surgery, remnant, cancerous cells. In another embodiment, a multi-kinase inhibitor is administered to a patient afflicted with thyroid cancer to induce iodine metabolizing genes in thyroid cancer cells.

In another embodiment, the method for sensitizing thyroid cancerous cells that are left after surgery comprises administering a multi-kinase inhibitor to a patient afflicted with thyroid cancer prior to surgery and administering radioactive iodine after surgery wherein, radioactive iodine inhibits the proliferation of the remaining cancerous cells. In another embodiment, the method for enhancing iodine metabolism in thyroid cancerous cells that are left after surgery comprises administering a multi-kinase inhibitor to a patient afflicted with thyroid cancer prior to surgery and administering radioactive iodine after surgery wherein, radioactive iodine inhibits the proliferation of the remaining cancerous cells.

In another embodiment, a patient as used herein is afflicted with cancer. In another embodiment, a patient as used herein is afflicted with a thyroid cancer. In another embodiment, a patient age of less than 45 or limited disease will have a full thyroidectomy. In another embodiment, surgery including laryngectomy is preformed in patient suffering from extracapsular spread of the disease. In another embodiment, the patient is treated with sorafenib ahead of surgery. In another embodiment, the disease can be partially or fully controlled by sorafenib. In another embodiment, treating a patient with sorafenib ahead of surgery results in a smaller operation. In another embodiment, patients with evidence of extracapsular spread undergo therapy with sorafenib as an adjuvant. In another embodiment, patients with evidence of extracapsular spread undergo therapy with sorafenib as an adjuvant after surgery. In another embodiment, patients with evidence of extracapsular spread are further treated with $^{131}$I. In another embodiment, patients treated with $^{131}$I have residual disease where the Thyroglobulin (tumor marker) does not reach 0 levels after treatment. In another embodiment, patients treated with $^{131}$I have residual disease benefit from therapy with sorafenib as an adjuvant. In another embodiment, therapy with sorafenib as an adjuvant decreases the risk for the development of recurrence of thyroid cancer. In another embodiment, therapy with sorafenib decreases the risk for the development of recurrence of thyroid cancer. In another embodiment, therapy with sorafenib in combination with an additional chemotherapeutic agent decreases the risk for the development of recurrence of thyroid cancer.

In another embodiment, a multi-kinase inhibitor, for example, sorafenib is used for treatment after surgery to treat occult cancer cells. In another embodiment, a multi-kinase inhibitor, for example, sorafenib treatment reduced cancer recurrences. In another embodiment, a multi-kinase inhibitor, for example, sorafenib reduced cancer recurrences due to occult cancer cells. In another embodiment, a multi-kinase inhibitor, for example, sorafenib treatment increases time to recurrence. In another embodiment, a multi-kinase inhibitor, for example, sorafenib treatment enhances tumor progression free survival post treatment with the compositions described herein. In another embodiment, a multi-kinase inhibitor, for example, sorafenib treatment leads to increased cure rate. In another embodiment, a multi-kinase inhibitor, for example, sorafenib treatment lead to increased overall survival.

In another embodiment, patients having positive lymph nodes undergo additional neck surgery to remove all the lymph nodes. In another embodiment, patients having positive lymph nodes are further treated with $^{131}$I as described hereinabove. In another embodiment, patients having positive lymph nodes that are further treated with sorafenib and $^{131}$I as described hereinabove have less chance for the development of recurrence of thyroid cancer. In another embodiment, adjuvant therapy with sorafenib decreases the chance of recurrence of thyroid cancer. In another embodiment, patients are treated with sorafenib and $^{131}$I to get rid of residual thyroid tissue. In another embodiment, patients are treated with sorafenib and $^{131}$I to treat any micrometastasis after surgery. In another embodiment, sorafenib enhances the effectiveness of radioactive iodine treatment in thyroid cancer patients. In another embodiment, sorafenib both enhances the effectiveness of radioactive iodine treatment in thyroid cancer patients and reduces tumor size. In another embodiment, sorafenib enhances radioactive iodine uptake by thyroid cells. In another embodiment, sorafenib enhances radioactive iodine uptake by thyroid cancer cells. In another embodiment, sorafenib enhances $^{131}$I uptake by thyroid cancer cells. In another embodiment, sorafenib acts synergistically with the $^{131}$I.

In another embodiment, patients having positive lymph nodes that are further treated with sorafenib and radioactive iodine as described hereinabove have less chance for the development of recurrence of thyroid cancer. In another embodiment, adjuvant therapy with sorafenib decreases the chance of recurrence of thyroid cancer. In another embodiment, patients are treated with sorafenib and radioactive iodine to get rid of residual thyroid tissue. In another embodiment, patients are treated with sorafenib and radioactive iodine to treat any micrometastasis after surgery. In another embodiment, sorafenib enhances radioactive iodine uptake by thyroid cancer cells. In another embodiment, sorafenib acts synergistically with the $^{131}$I.

In another embodiment, patients with recurrence in the neck are treated with additional surgery or external beam radiation. In another embodiment, sorafenib is used to treat these patients and save them the morbidity of extensive surgery and/or external beam radiation. In another embodiment, patients that develop metastatic disease outside of the neck that is iodine-avid benefit from the synergistic activity of sorafenib with radioactive iodine. In another embodiment, sorafenib is used as a therapeutic modality to treat a metastatic thyroid cancer.

In another embodiment, the patient further undergoes remnant ablation to destroy any remaining normal thyroid tissue as source of Tg production and RAI uptake, allowing earlier detection of recurrence. In another embodiment, the patient further undergoes adjuvant therapy to ablate any remaining postsurgical microscopic thyroid cancer in remnant or lymph nodes/metastases which may decrease recurrence and mortality rates.

In another embodiment, radioiodine ablation is performed in patients with stages III and IV disease (AJCC sixth edition), all patients with stage II disease younger than age 45 years and most patients with stage II disease 45 years or older, and selected patients with stage I disease, especially those with multifocal disease, nodal metastases, extrathyroidal or vascular invasion, and/or more aggressive histologies.

In one embodiment, provided herein is a method of improving radiotherapy in a subject having a bulky disease, whereby the treatment of the bulky disease based on radioactive iodine in a subject, comprising the step of administering to said subject a composition comprising a multi-kinase inhibitor, thereby improving a radiotherapy in a subject having a bulky disease. In another embodiment, the term "bulky disease" refers to a paraneoplastic disease presenting with a tumor beyond a critical size. In one embodiment, staging of various cancer, such as thyroid cancer in one embodiment, or (primary) liver cancer, prostate cancer, NHL, melanoma, lung cancer, breast cancer and the like in other discrete embodiments, use tumor size as a factor of the staging. In one embodiment, TNM is the method most universally used as the staging method and applies to both papillary and follicular thyroid cancers. The T in TNM refers in one embodiment to: Tumor size (in cm), wherein T=1 if the tumor is less than 1 cm; T=2 if it is 1-4 cm; T=3 if it is greater than 4 cm. bulky disease refers in one embodiment to thyroid cancer, either primary or metastatic with stage 2 and above on the TNM staging method. In one embodiment, the bulky disease treated using the methods and compositions described herein is non-Hodgkin's Lymphoma (NHL). In another embodiment the bulky disease is prostate adenocarcinoma, or breast cancer, or liver cancer in other discrete embodiments of the tumor associated bulky diseases treated, inhibited or suppressed or otherwise whose symptoms are ameliorated using the methods described herein.

In one embodiment, the bulky disease treated using the methods described herein is bulky lymphadenopathy, referring in another embodiment to a condition wherein the lymph node diameter≥5 cm. In one embodiment, bulky lymphadenopathy is predictive of a high incidence of relapse/progression of chronic lymphocytic leukemia (CLL) in a subject. In another embodiment, treating a subject having bulky lymphoadenopathy using the methods and compositions described herein, reduces the probability of relapse or inhibits progression of CLL.

In another embodiment, using the methods and compositions described herein improves outcomes of radioimmunotherapy (RIT) in patients with bulky, rapidly progressive and aggressive histologies in NHL In another embodiment, the methods described herein encompass the use of other radio label such as in one embodiment an isotope in combination with sorafenib in the treatment of bulky diseases. These radioisotopes are in another embodiment $^{82}$Yttrium, $^{83}$Yttrium, $^{84}$Yttrium, $^{85}$Yttrium, $^{86}$Yttrium, $^{87}$Yttrium, $^{88}$Yttrium, $^{90}$Yttrium, $^{91}$Yttrium, $^{92}$Yttrium, $^{93}$Yttrium, $^{94}$Yttrium, $^{95}$Yttrium, $^{96}$Yttrium, or their combination. In one embodiment, provided herein is a method of enhancing Yttrium absorption in a bulky lymphoadenoma in a subject, comprising the step of administering to said subject a composition comprising a multi-kinase inhibitor thereby enhancing Yttrium absorption in the lymphoadenoma in a subject. In another embodiment, provided herein is a method of treating a non radiyttrium-avid Bulky Non-Hodgkin's Lymphoma in a subject, comprising the step of enhancing Yttrium absorption in a bulky lymphoadenoma in said subject by administering to said subject a composition comprising a multi-kinase inhibitor, thereby treating a Bulky Non-Hodgkin's Lymphoma in the subject. In one embodiment, the multi-kinase inhibitor used in the methods of treating a bulky disease is sorafenib. In one embodiment, provided herein is a method of improving a medical diagnostic or therapeutic procedure for a bulky disease based on radioactive isotope in a subject, comprising the step of administering to said subject a composition comprising a multi-kinase inhibitor, thereby improving a medical diagnostic or therapeutic procedure based on radioactive isotope in a subject. In another embodiment, the radioisotope is iodine, or Yttrium in another embodiment. In another embodiment, the therapeutic procedure is radioimmunotherapy (RIT).

In another embodiment, provided herein is a method of improving a medical diagnostic procedure based on radioactive iodine in a subject, comprising the step of administering to said subject a composition comprising a multi-kinase inhibitor, thereby improving said medical diagnostic procedure based on radioactive iodine in said subject. In another embodiment, provided herein is a method of improving the resolution of a medical diagnostic procedure based on radioactive iodine in a subject, comprising the step of administering to said subject a composition comprising a multi-kinase inhibitor, thereby improving said medical diagnostic procedure based on radioactive iodine in said subject.

In another embodiment, provided herein is a method of minimizing the rate of false negative results of a medical diagnostic procedure based on radioactive iodine in a subject, comprising the step of administering to a subject a composition comprising a multi-kinase inhibitor, thereby improving a medical diagnostic procedure based on radioactive iodine in a subject. In another embodiment, provided herein a method of enhancing iodine metabolism in a thyroid cell, thereby minimizing the rate of false negative results of a medical diagnostic procedure based on radioactive iodine in a subject, comprising the step of administering to a subject a composition comprising a multi-kinase inhibitor, thereby improving a medical diagnostic procedure based on radioactive iodine in a subject. In another embodiment, provided herein a method of enhancing iodine metabolism in a cancerous thyroid cell, thereby minimizing the rate of false negative results of a medical diagnostic procedure based on radioactive iodine in a subject, comprising the step of administering to a subject a composition comprising a multi-kinase inhibitor, thereby improving a medical diagnostic procedure based on radioactive iodine in a subject. In another embodiment, provided herein is a method of enhancing iodine metabolism in a thyroid cell, thereby minimizing the rate of false negative results of a medical diagnostic procedure based on radioactive iodine in a subject, comprising the step of administering to a subject a composition comprising a multi-kinase inhibitor and radioactive iodine, thereby improving a medical diagnostic procedure based on radioactive iodine in a subject. In another embodiment, provided herein a method of enhancing iodine metabolism in a thyroid cell, thereby minimizing the rate of false negative results of a medical diagnostic procedure based on radioactive iodine in a subject, comprising the step of administering to a subject a composition comprising a multi-kinase inhibitor followed by administering to a subject a composition comprising radioactive iodine, thereby improving a medical diagnostic procedure based on radioactive iodine in a subject.

In another embodiment, provided herein is a method of enhancing the sensitivity of a medical diagnostic procedure based on radioactive iodine in a subject, comprising the step of administering to a subject a composition comprising a multi-kinase inhibitor, thereby enhancing the sensitivity of a medical diagnostic procedure based on radioactive iodine in a subject. In another embodiment, provided herein a method of enhancing the sensitivity of a medical diagnostic procedure based on radioactive iodine in a subject, comprising the step of administering to a subject a composition comprising a multi-kinase inhibitor, thereby enhancing the sensitivity of a medical diagnostic procedure based on radioactive iodine in a subject. In another embodiment, provided herein a method of enhancing the sensitivity of a medical diagnostic procedure based on radioactive iodine in a subject, comprising the step of administering to a subject a composition comprising a multi-kinase inhibitor, thereby improving a medical diagnostic procedure based on radioactive iodine in a subject. In another embodiment, a method of enhancing the sensitivity of a medical diagnostic procedure comprises the ability to induce iodine metabolism in a thyroid cell. In another embodiment, a method of enhancing the sensitivity of a medical diagnostic procedure comprises the ability to induce iodine metabolism in a thyroid cancer cell. In another embodiment, a method of enhancing the sensitivity of a medical diagnostic procedure comprises the ability to administer reduced amounts of iodine to a subject undergoing a medical diagnostic procedure.

In another embodiment, provided herein is a method of improving a thyroid nuclear medicine scan. In another embodiment, provided herein a method of improving an imaging procedure to evaluate the thyroid gland. In another embodiment, provided herein a method of improving a radionuclide scan, a radioactive tracer that is selectively absorbed by the thyroid. In another embodiment provided herein a method of improving an imaging procedure to detect radioactive emissions from the thyroid. In another embodiment provided herein a method of improving an imaging procedure to measure the concentration of the radioactive tracer in the thyroid gland.

In another embodiment provided herein is a method of improving an imaging procedure for thyroid scans performed to determine the size, shape, location, and relative function of the thyroid gland. In another embodiment provided herein a method of improving an imaging procedure for diagnosing the cause of thyrotoxicosis. In another embodiment provided herein a method of improving an imaging procedure for assessment of a goiter. In another embodiment provided herein a method of improving an imaging procedure for detecting the presence of ectopic thyroid tissue.

In another embodiment, provided herein a method of improving the evaluation of the filtration rate of kidneys. In another embodiment, provided herein a method of improving the evaluation of the filtration rate of kidneys with Iodine-125. In another embodiment, provided herein a method of improving diagnosis of deep vein thrombosis in the leg. In another embodiment, provided herein a method of improving diagnosis of deep vein thrombosis in the leg with Iodine-125.

In another embodiment, provided herein is a method of improving imaging of the thyroid. In another embodiment, provided herein a method of improving imaging of the thyroid with Iodine-131. In another embodiment, provided herein a method of improving diagnosis of abnormal liver function. In another embodiment, provided herein a method of improving diagnosis of abnormal liver function with Iodine-131. In another embodiment, provided herein a method of improving diagnosis of renal blood flow. In another embodiment, provided herein a method of improving diagnosis of renal blood flow with Iodine-131. In another embodiment, provided herein a method of improving diagnosis of urinary tract obstruction.

In another embodiment, provided herein is a method of improving Whole body scans (WBS). In another embodiment, provided herein a method of improving WBS with Iodine-131. In another embodiment, provided herein a method of improving WBS for detection of occult disease. In another embodiment, provided herein a method of improving WBS for detection of a disease that is amenable to RAI therapy. In another embodiment, provided herein a method of improving FDG-PET scanning in thyroid cancer. In another embodiment, provided herein a method of improving FDG-PET scanning of occult metastatic disease in patients with elevated serum thyroglobulin sTG in the setting of a negative whole body I-131 scan.

In another embodiment, a patient is diagnosed with a thyroid nodule—workup entails ultrasound (US), and/or radioactive WBS. In another embodiment, fine needle aspirate biopsy (FNA) further proves the diagnosis, or suggests that there may be a malignancy. In another embodiment, WBS is used throughout treatment as a diagnostic scan. In another embodiment, sorafenib is used to enhance the sensitivity of this modality. In another embodiment, sorafenib is used to enhance the specificity of this test.

In another embodiment, a patient has additional staging to determine the extent of the disease. In another embodiment, Lymph nodes are evaluated. In another embodiment, positive, infected, lymph nodes are removed at surgery. In another embodiment, MRI and/or CT of the neck is used to evaluate the extent of the disease.

In another embodiment, provided herein is a method of improving modalities for the evaluation of thyroid cancer patients include $^{124}$I PET/CT. In another embodiment, provided herein a method of improving the signal-to-noise ratio and the high count sensitivity of positron emission imaging. In another embodiment, provided herein a method of improving DCE-MRI of tumor lesions.

In another embodiment, provided herein is a method of improving RAIU. In another embodiment, provided herein a method of improving RAIU with I-123. In another embodiment, provided herein a method of improving thyroid scintigraphy. In another embodiment, the dose used for uptake is about 0.05 to 0.6 mCi and for scanning about 0.1 to 0.6 mCi.

In another embodiment, provided herein is a method of improving the evaluation and/or diagnosis of Graves' hyperthyroidism. In another embodiment, provided herein a method of improving RAIU test to differentiate postpartum, silent, or subacute thyroiditis from Graves' hyperthyroidism. In another embodiment, provided herein a method of improving RAIU test to differentiate postpartum, silent, or subacute thyroiditis from Graves' hyperthyroidism in patients with suppressed thyrotropin (TSH) levels.

In another embodiment, provided herein is a method of improving thyroid scintigraphy for visualizing the thyroid gland's structure. In another embodiment, provided herein a method of improving thyroid scintigraphy for localizing functioning thyroid tissue elsewhere in the body.

In another embodiment, provided herein is a medical diagnostic test comprising radioactive iodine and a multi-kinase inhibitor. In another embodiment, the multi-kinase inhibitor is Sorafenib. In another embodiment, the radioactive iodine is $^{131}$I, $^{123}$I, or a combination thereof.

In another embodiment, provided herein is a method of providing prognosis on the efficacy of treatment of metastatic thyroid cancer with a multi-kinase inhibitor. In another embodiment, provided herein a method for determining the efficacy of sorafenib in patients with metastatic thyroid carcinoma. In another embodiment, provided herein a method for evaluating the objective response and stable disease rate in patients receiving sorafenib. In another embodiment, provided herein a method of providing prognosis on the efficacy of treatment of metastatic thyroid cancer with a multi-kinase inhibitor comprising the use of tests such TSH measurement and sTG measurement prior to the start of treatment with a multi-kinase inhibitor, and at time points after the beginning of treatment with a multi-kinase inhibitor. In another embodiment, these test provide direct and indirect insight into the progression of the disease.

In another embodiment, provided herein is a method of providing prognosis on the efficacy of treatment of metastatic thyroid cancer with a multi-kinase inhibitor comprising the use of imaging modalities. In another embodiment, provided herein is a method of providing prognosis on the efficacy of treatment of metastatic thyroid cancer with a multi-kinase inhibitor comprising monitoring sTG levels in patients. In another embodiment, provided herein a method of providing prognosis on the efficacy of treatment of metastatic thyroid cancer with a multi-kinase inhibitor comprising monitoring TSH levels in patients. In another embodiment, provided herein a method of providing prognosis on the efficacy of treatment of metastatic thyroid cancer with a multi-kinase inhibitor comprising performing histocytometry for molecular markers of the PI3K/AKT and RAS/RAF/MEK/ERK signaling pathways and tumor differentiation on archived specimens obtained from the patients prior to and while on treatment. In another embodiment, provided herein a method for providing prognosis on the efficacy of treatment of metastatic thyroid cancer with a multi-kinase inhibitor comprising performing DCE-MRI on patients.

In another embodiment, provided herein that initial shrinkage in thyroid tumor size that occurs in patients in the first two to four months of therapy is mediated primarily through antivascular effects of a multi-kinase inhibitor. In another embodiment, provided herein that subsequent increase in sTG levels (in patients where there is no evidence of tumor progression) is indicative of re-expression of thyroid hormone metabolizing genes in response to sustained inhibition of RAF-MEK-ERK activity. In another embodiment, provided herein that a multi-kinase inhibitor is an active agent for DTC. In another embodiment, provided herein that a multi-kinase inhibitor mediates its cytoreductive effect through inhibition in Tumor cells (TC) and/or endothelial cells (EC) in thyroid cancer. In another embodiment a method of providing prognosis on the efficacy of treatment of metastatic thyroid cancer with a multi-kinase comprises measuring RAF/MEK/ERK activation. In another embodiment a method of providing prognosis on the efficacy of treatment of metastatic thyroid cancer with a multi-kinase comprises measuring p-ERK in EC.

In another embodiment, $^{124}$I-Iodide PET in thyroid cancer characterizes and guides cancer therapy in differentiated thyroid cancer (FIG. 14). In another embodiment, PET scans are quantitative, yielding images directly in terms of activity concentration (mCi/ml). In another embodiment, decrease in FDG-PET uptake at two-six weeks shows early response to sorafenib. In another embodiment, decrease in FDG-PET uptake at three-five weeks shows early response to sorafenib. In another embodiment, decrease in FDG-PET uptake at four weeks shows early response to sorafenib (FIGS. 12 and 13).

In another embodiment, provided herein early CT (8 weeks) for early detection of tumor volume. In another embodiment, provided herein early and late CT (8 weeks and 6 months) for the assessing of durable decrease in tumor volume (FIG. 15).

The inhibitors of the present invention and pharmaceutical compositions comprising same can be, in another embodiment, administered to a subject by any method known to a person skilled in the art, such as parenterally, paracancerally, transmucosally, transdermally, intramuscularly, intravenously, intra-dermally, subcutaneously, intra-peritonealy, intra-ventricularly, intra-cranially, intra-vaginally or intra-tumorally.

In another embodiment of methods and compositions of the present invention, the pharmaceutical compositions are administered orally, and are thus formulated in a form suitable for oral administration, i.e. as a solid or a liquid preparation. Suitable solid oral formulations include tablets, capsules, pills, granules, pellets and the like. Suitable liquid oral formulations include solutions, suspensions, dispersions, emulsions, oils and the like. In another embodiment of the present invention, the active ingredient is formulated in a capsule. In accordance with this embodiment, the compositions of the present invention comprise, in addition to the active compound (e.g. the mimetic compound, peptide or nucleotide molecule) and the inert carrier or diluent, a hard gelating capsule.

In another embodiment, the pharmaceutical compositions are administered by intravenous, intra-arterial, or intra-muscular injection of a liquid preparation. Suitable liquid formulations include solutions, suspensions, dispersions, emulsions, oils and the like. In another embodiment, the pharmaceutical compositions are administered intravenously and are thus formulated in a form suitable for intravenous administration. In another embodiment, the pharmaceutical compositions are administered intra-arterially and are thus formulated in a form suitable for intra-arterial administration. In another embodiment, the pharmaceutical compositions are administered intra-muscularly and are thus formulated in a form suitable for intra-muscular administration.

In another embodiment, the pharmaceutical compositions are administered topically to body surfaces and are thus formulated in a form suitable for topical administration. Topical formulations include, in another embodiment, gels, ointments, creams, lotions, drops and the like.

In another embodiment, the pharmaceutical composition is administered as a suppository, for example a rectal suppository or a urethral suppository. In another embodiment, the pharmaceutical composition is administered by subcutaneous implantation of a pellet. In another embodiment, the pellet provides for controlled release of active agent over a period of time.

In another embodiment, the active compound is delivered in a vesicle, e.g. a liposome.

In other embodiments, carriers or diluents used in methods of the present invention include, but are not limited to, a gum, a starch (e.g. corn starch, pregeletanized starch), a sugar (e.g., lactose, mannitol, sucrose, dextrose), a cellulosic material (e.g. microcrystalline cellulose), an acrylate (e.g. polymethylacrylate), calcium carbonate, magnesium oxide, talc, or mixtures thereof.

In other embodiments, pharmaceutically acceptable carriers for liquid formulations are aqueous or non-aqueous solutions, suspensions, emulsions or oils. Examples of non-aqueous solvents are propylene glycol, polyethylene glycol, and injectable organic esters such as ethyl oleate. Aqueous carriers include water, alcoholic/aqueous solutions, emulsions or suspensions, including saline and buffered media. Examples of oils are those of animal, vegetable, or synthetic origin, for example, peanut oil, soybean oil, olive oil, sunflower oil, fish-liver oil, another marine oil, or a lipid from milk or eggs.

In another embodiment, parenteral vehicles (for subcutaneous, intravenous, intra-arterial, or intramuscular injection) include sodium chloride solution, Ringer's dextrose, dextrose and sodium chloride, lactated Ringer's and fixed oils. Intravenous vehicles include fluid and nutrient replenishers, electrolyte replenishers such as those based on Ringer's dextrose, and the like. Examples are sterile liquids such as water and oils, with or without the addition of a surfactant and other pharmaceutically acceptable adjuvants. In general, water, saline, aqueous dextrose and related sugar solutions, and glycols such as propylene glycols or polyethylene glycol are preferred liquid carriers, particularly for injectable solutions. Examples of oils are those of animal, vegetable, or synthetic origin, for example, peanut oil, soybean oil, olive oil, sunflower oil, fish-liver oil, another marine oil, or a lipid from milk or eggs.

In other embodiments, the compositions further comprise binders (e.g. acacia, cornstarch, gelatin, carbomer, ethyl cellulose, guar gum, hydroxypropyl cellulose, hydroxypropyl methyl cellulose, povidone), disintegrating agents (e.g. cornstarch, potato starch, alginic acid, silicon dioxide, croscarmelose sodium, crospovidone, guar gum, sodium starch glycolate), buffers (e.g., Tris-HCl., acetate, phosphate) of various pH and ionic strength, additives such as albumin or gelatin to prevent absorption to surfaces, detergents (e.g., Tween 20, Tween 80, Pluronic F68, bile acid salts), protease inhibitors, surfactants (e.g. sodium lauryl sulfate), permeation enhancers, solubilizing agents (e.g., glycerol, polyethylene glycerol), anti-oxidants (e.g., ascorbic acid, sodium metabisulfite, butylated hydroxyanisole), stabilizers (e.g. hydroxypropyl cellulose, hyroxypropylmethyl cellulose), viscosity increasing agents (e.g. carbomer, colloidal silicon dioxide, ethyl cellulose, guar gum), sweeteners (e.g. aspartame, citric acid), preservatives (e.g., Thimerosal, benzyl alcohol, parabens), lubricants (e.g. stearic acid, magnesium stearate, polyethylene glycol, sodium lauryl sulfate), flowaids (e.g. colloidal silicon dioxide), plasticizers (e.g. diethyl phthalate, triethyl citrate), emulsifiers (e.g. carbomer, hydroxypropyl cellulose, sodium lauryl sulfate), polymer coatings (e.g., poloxamers or poloxamines), coating and film forming agents (e.g. ethyl cellulose, acrylates, polymethacrylates) and/or adjuvants. Each of the above excipients represents a separate embodiment of the present invention.

In another embodiment, the pharmaceutical compositions provided herein are controlled-release compositions, i.e. compositions in which the active compound is released over a period of time after administration. Controlled- or sustained-release compositions include formulation in lipophilic depots (e.g. fatty acids, waxes, oils). In another embodiment, the composition is an immediate-release composition, i.e. a composition in which of the active compound is released immediately after administration.

In another embodiment, the pharmaceutical composition is delivered in a controlled release system. For example, the agent may be administered using intravenous infusion, an implantable osmotic pump, a transdermal patch, liposomes, or other modes of administration. In one embodiment, a pump may be used (see Langer, supra; Sefton, CRC Crit. Ref. Biomed. Eng. 14:201 (1987); Buchwald et al., Surgery 88:507 (1980); Saudek et al., N. Engl. J. Med. 321:574 (1989). In another embodiment, polymeric materials are used; e.g. in microspheres in or an implant. In yet another embodiment, a controlled release system is placed in proximity to the target cell, thus requiring only a fraction of the systemic dose (see, e.g., Goodson, in Medical Applications of Controlled Release, supra, vol. 2, pp. 115-138 (1984); and Langer R, Science 249: 1527-1533 (1990).

The compositions also include, in another embodiment, incorporation of the active material into or onto particulate preparations of polymeric compounds such as polylactic acid, polglycolic acid, hydrogels, etc, or onto liposomes, microemulsions, micelles, unilamellar or multilamellar vesicles, erythrocyte ghosts, or spheroplasts.) Such compositions will influence the physical state, solubility, stability, rate of in vivo release, and rate of in vivo clearance.

Also included in the present invention are particulate compositions coated with polymers (e.g. poloxamers or poloxamines) and the compound coupled to antibodies directed against tissue-specific receptors, ligands or antigens or coupled to ligands of tissue-specific receptors.

Also comprehended by the invention are compounds modified by the covalent attachment of water-soluble polymers such as polyethylene glycol, copolymers of polyethylene glycol and polypropylene glycol, carboxymethyl cellulose, dextran, polyvinyl alcohol, polyvinylpyrrolidone or polyproline. The modified compounds are known to exhibit substantially longer half-lives in blood following intravenous injection than do the corresponding unmodified compounds (Abuchowski et al., 1981; Newmark et al., 1982; and Katre et al., 1987). Such modifications may also increase the compound's solubility in aqueous solution, eliminate aggregation, enhance the physical and chemical stability of the compound, and greatly reduce the immunogenicity and reactivity of the compound. As a result, the desired in vivo biological activity may be achieved by the administration of such polymer-compound abducts less frequently or in lower doses than with the unmodified compound.

Each of the above additives, excipients, formulations and methods of administration represents a separate embodiment of the present invention.

In one embodiment, the methods of the present invention comprise administering an active compound as the sole active ingredient. However, also encompassed within the scope of the present invention are methods for treating diseases and disorders that comprise administering the active compound in combination with one or more therapeutic agents. These agents include, but are not limited to, chemotherapeutic agents. In another embodiment, these agents are appropriate for the disease or disorder that is being treated, as is well known in the art.

In one embodiment, the methods of the present invention comprise administering an active compound as the sole active ingredient. However, also encompassed within the scope of the present invention are methods for treating diseases and disorders that comprise administering the active compound in combination with one or more therapeutic agents.

The methods described herein comprise in one embodiment, using a combination therapy. In another embodiment, the term "combination" is used in its broadest sense and means that a subject is treated with at least two therapeutic regimens. In one embodiment, "combination therapy" refers to a subject who is treated with at least two oncotherapeutic regimens, such as in another embodiment, with at least sorafenib or biologically active variant thereof in combination with at least one therapeutically radioactive isotope, but the timing of administration of the different oncotherapeutic regimens can be varied so long as the beneficial effects of the combination of these two therapeutic agents is achieved.

Treatment with Sorafenib in combination with a therapeutically radioactive isotope can be simultaneous (concurrent), consecutive (sequential, in either order), or a combination thereof. Therefore, in one embodiment, a subject undergoing combination therapy receives treatment with both of these therapeutic agents at the same time (i.e., simultaneously) or at different times (i.e., sequentially, in either order, on the same day, or on different days), so long as the therapeutic effect of the combination of both substances is caused in the subject undergoing therapy. In some embodiments, the combination of Sorafenib or biologically active variant thereof and therapeutically radioactive isotope, such as iodine in one embodiment or yttrium in another embodiment, will be given simultaneously for one dosing, but other dosings will include sequential administration, in either order, on the same day, or on different days. Sequential administration may be performed regardless of whether the subject responds to the first therapeutic agent administered. Where these two therapeutic agents are administered simultaneously, they can be administered as separate pharmaceutical compositions, each comprising either the Sorafenib (or another multi-kinase inhibitor) or the therapeutically radioactive isotope, such as iodine in one embodiment or yttrium in another embodiment, or they can be administered as a single pharmaceutical composition comprising both of these therapeutic agents.

The effect of the combination therapy can also be optimized by varying the timing of administration of either Sorafenib (or another multi-kinase inhibitor) and/or the therapeutically radioactive isotope, such as iodine in one embodiment or yttrium in another embodiment. Thus, in some embodiments, the Sorafenib (or biologically active variant thereof, such as a substituted diphenyl, quinolyl, isoquinolyl, pyridyl urea or their combination) is administered simultaneously with the therapeutically radioactive isotope, such as iodine in one embodiment or yttrium in another embodiment. In other embodiments, the Sorafenib is administered first and then the therapeutically radioactive isotope, is administered next. In yet other embodiments, the therapeutically radioactive isotope, such as iodine in one embodiment or yttrium in another embodiment, is administered first, and the Sorafenib (or another multi-kinase inhibitor) is administered next. In some embodiments, the combination of Sorafenib (or another multi-kinase inhibitor) and the therapeutically radioactive isotope, such as iodine in one embodiment or yttrium in another embodiment., are given concurrently for one dosing, but other dosings can include sequential administration, in either order, on the same day, or on different days. In one embodiment, where the Sorafenib (or another multi-kinase inhibitor) and the therapeutically radioactive isotope, are administered simultaneously, they are administered as separate pharmaceutical compositions, each comprising either the Sorafenib (or another multi-kinase inhibitor) or the therapeutically radioactive isotope, or can be administered as a single pharmaceutical composition comprising both of these therapeutic agents.

Therapy with an effective amount of the combination of Sorafenib (or another multi-kinase inhibitor) and the therapeutically radioactive isotope promotes a positive therapeutic response for a differentiated thyroid cancer such as follicular or papillary differentiated thyroid cancer or NHL in other embodiments. Concurrent therapy with both of these agents potentiates the anti-tumor activity of each of these agents, thereby providing a positive therapeutic response that is improved with respect to that observed with administration of Sorafenib (or another multi-kinase inhibitor) alone or administration of therapeutically radioactive isotope alone. Improvement of the positive therapeutic response may be additive in nature or synergistic in nature. Where synergistic, concurrent therapy with Sorafenib (or another multi-kinase inhibitor) and at least one therapeutically radioactive isotope, such as iodine in one embodiment or yttrium in another embodiment results in a positive therapeutic response that is greater than the sum of the positive therapeutic responses achieved with the separate components.

In one embodiment, the treatment is accomplished with varying doses as well as dosing regimens, as long as the combination of these doses is effective at treating any one or more of a number of therapeutic parameters. These treatment regimens are based in another embodiment on doses and dosing schedules that maximize therapeutic effects, such as those described below. Those skilled in the art recognize that a dose of Sorafenib may not be therapeutically effective when administered individually, but will be therapeutically effective when administered in combination with the other agent. Thus, in some embodiments, the therapeutically effective dose of a combination of Sorafenib and therapeutically radioactive isotope may comprise doses of individual active agents that, when administered alone, would not be therapeutically effective or would be less therapeutically effective than when administered in combination with each other.

Because the combined administration of these two therapeutic agents potentiates the effectiveness of both of these agents, a positive therapeutic response that is similar to that achieved with a particular dose of Sorafenib alone can be achieved with lower doses of this agent. The significance of this is two-fold. First, the potential therapeutic benefits of treatment of thyroid cancer with Sorafenib or variant thereof can be realized at doses that minimize toxicity responses normally associated with high-dose Sorafenib administration. Such toxicity responses include, but are not limited to, Rash, Hand-foot syndrome (Palmar-plantar erythrodysesthesia or PPE)—skin rash, swelling, redness, pain and/or peeling of the skin on the palms of hands and soles of feet, diarrhea, Fatigue, High blood pressure, Hair loss (i.e. thinning or patchy hair loss), Nausea, Itching, Low white blood cell count, Poor appetite, Vomiting, Bleeding, Increased amylase/lipase blood counts, Low phosphorus level, Constipation, Shortness of breath, Cough, Numbness, tingling or pain in hands and feet., Low platelet count, Dry skin, Abdominal pain, Bone, muscle, joint pain, Headache, Weight loss, or heart attack and their combination.

In one embodiment, the dose of a therapeutically radioactive isotope, such as iodine in one embodiment or yttrium in another embodiment, to be administered in combination with an amount of Sorafenib (or another multi-kinase inhibitor) and the amount of either of these therapeutic agents needed to potentiate the effectiveness of the other therapeutic agent are readily determined. Factors influencing the mode of administration and the respective amount of Sorafenib (or another multi-kinase inhibitor) and therapeutically radioactive isotope administered in combination the particular lymphoma or solid tumor undergoing therapy in one embodiment, the severity of the disease in another embodiment, the history of the disease in another embodiment, and the age, height, weight, health, and physical condition of the individual undergoing therapy in other discrete embodiments of the compositions methods and tests described herein. In one embodiment, the amount of these therapeutic agents to be administered in combination therapy will be dependent upon the mode of administration and whether the subject will undergo a single dose or multiple doses of each of these therapeutic agents. Generally, a higher dosage of the antibody agent is preferred with increasing weight of the subject undergoing therapy.

In some embodiments, combination therapy is achieved by administering recommended total weekly doses of a pharmaceutical composition comprising Sorafenib (or another multi-kinase inhibitor) in combination with recommended therapeutically effective doses of a therapeutically radioactive isotope, each being administered according to a particular dosing regimen. In one embodiment, the term "therapeutically effective dose or amount" refers to an amount of one of these two therapeutic agents that, when administered with a therapeutically effective dose or amount of the other of these two therapeutic agents, brings about a positive therapeutic response with respect to treatment of cancers. As noted, administration of the separate pharmaceutical compositions can be at the same time or at different times, so long as the therapeutic effect of the combination of both substances is caused in the subject undergoing therapy.

In another embodiment, the subject undergoing treatment with one or more weekly doses of therapeutically radioactive isotope is also administered Sorafenib (or another multi-kinase inhibitor) as described herein below according to a constant Sorafenib dosing regimen or according to a two-level Sorafenib (or another multi-kinase inhibitor) dosing regimen. An aspect of this combination therapy is in another embodiment, an overlapping period of time during which both of these therapeutic agents are being administered to the subject, each according to the particular dosing regimen disclosed. In one embodiment, where combination therapy comprises this overlapping time period of dosing with these two therapeutic agents, the combination therapy is also referred to as "concurrent therapy." The first therapeutically effective dose administered to the subject can be the therapeutically radioactive isotope, such as iodine in one embodiment or yttrium in another embodiment, or can be the Sorafenib (or another multi-kinase inhibitor). On those days where both therapeutically radioactive isotope and Sorafenib (or another multi-kinase inhibitor) are scheduled to be administered to the subject, these therapeutic agents can be administered either at the same time (i.e., simultaneous administration) or at different times (i.e., sequential administration, in either order). Although the following embodiments of dosing regimens refers to dosing of therapeutically radioactive isotope as described herein in combination with Sorafenib as described herein, it is recognized that the protocols (i.e., initiation of treatment, duration of isotope and multi-kinase inhibitor treatment, radioactive isotope and multi-kinase inhibitor dosing regimens, interruption of multi-kinase inhibitor dosing, subsequent courses of combination multi-kinase inhibitor/radioactive isotope therapy, multi-kinase inhibitor dosing schedule, and the like) are equally applicable to dosing with $^{131}$I or $^{90}$Y as described herein in combination with Sorafenib as described herein, dosing with a therapeutically radioactive isotope as described herein in combination with multi-kinase inhibitor as described herein, or dosing with therapeutically radioactive isotope as described herein in combination with multi-kinase inhibitor.

Where concurrent therapy with Sorafenib (or another multi-kinase inhibitor) and therapeutically effective radioisotope, such as $^{131}$I in one embodiment or $^{90}$Y in another embodiment comprises one or more cycles of a constant Sorafenib (or another multi-kinase inhibitor) dosing regimen, the initial therapeutic agent to be administered to the subject at the start of a treatment period can be either the Sorafenib (or another multi-kinase inhibitor) or the therapeutically radioactive isotope, so long as the subject has an overlapping period of time during which both therapeutic agents are being administered to the subject, each according to the particular dosing regimen disclosed.

Thus, in one embodiment, concurrent therapy with these two therapeutic agents comprises initiating the constant Sorafenib (or another multi-kinase inhibitor) dosing regimen prior to initiating administration of therapeutically effective doses of radioactive isotope, which are administered weekly, or, alternatively, once every two, three, or four weeks, up to two months in certain embodiments. In this manner, a first dose of Sorafenib (or another multi-kinase inhibitor) is administered up to one month before the first dose of therapeutically radioactive isotope is administered. The term "up to two month" refers in one embodiment to the fact that the first dose of Sorafenib (or another multi-kinase inhibitor) is administered at least one day before initiating therapeutically radioactive isotope administration, but not more than one month (i.e., 30 days) before initiating therapeutically radioactive isotope administration. Thus, Sorafenib administration can begin, for example, 1 day, 2 days, 3 days, 4 days, 5 days, 6 days, 7 days (i.e., 1 week), 10 days, 14 days (i.e., two weeks), 17 days, 21 days (i.e., 3 weeks), 24 days, 28 days (4 weeks), or up to two months (i.e., 60 or 62 days) before administering the first therapeutically effective dose of the radioactive isotope.

In other embodiments, the constant Sorafenib (or another multi-kinase inhibitor) dosing regimen and therapeutically radioactive isotope administration begin concurrently on the same day, either at the same time (i.e., simultaneous administration) or at different times (i.e., sequential administration, in either order). Thus, for example, in one embodiment where concurrent therapy with these two therapeutic agents begins on day 1 of a treatment period, a first therapeutically effective dose of $^{131}$I and a first dose of Sorafenib would both be administered on day 1 of this treatment period. In one such embodiment, the dose of $^{131}$I is administered first, followed by administration of the dose of Sorafenib (or another multi-kinase inhibitor) within about 10 minutes to about 4 hours of the completion of administering the dose of therapeutically radioactive isotope, such as within about 10 minutes in one embodiment, or 15, 20, 25, 30, 45, 60, 90, 120, 150, 180, 210, 240 minutes and so on in other discrete embodiments of the administration regimens used.

In another embodiment, the initial therapeutic agent to be administered to the subject at the start of a treatment period is the therapeutically radioactive isotope, while the first cycle of constant Sorafenib (or another multi-kinase inhibitor) dosing is initiated by administering a first dose of Sorafenib (or another multi-kinase inhibitor) subsequently, in another embodiment, within 10 days following administration of the first therapeutically effective dose of the radioactive isotope, or within 1, 2, 3, 4, 5, 6, 7, 8, 9, or 10 days in other discrete embodiments. In some embodiments, the first cycle of constant Sorafenib (or another multi-kinase inhibitor) dosing is initiated by administering a first dose of Sorafenib (or another multi-kinase inhibitor) within 7 days of administering the first therapeutically effective dose of radioactive isotope, such as within 1 day in one embodiment, or 2, 3, 4, 5, 6, or 7 days in other embodiments. Thus, in one embodiment, a therapeutically effective dose of the radioactive isotope is administered on day 1 of a treatment period, and the first cycle of constant Sorafenib (or another multi-kinase inhibitor) dosing is initiated 7 days later, i.e., by administering the initial dose of Sorafenib (or another multi-kinase inhibitor) on day 8 of the treatment period.

In one embodiment, following completion of the first cycle of constant Sorafenib (or another multi-kinase inhibitor) dosing, a subject receiving therapeutically effective doses of the radioactive isotope accordingly to a weekly dosing schedule, or, in other embodiments, once every two, three, four or eight weeks, is administered one or more subsequent cycles of constant Sorafenib (or another multi-kinase inhibitor) dosing. During the second and all subsequent cycles of constant Sorafenib (or another multi-kinase inhibitor) dosing, generally the first therapeutic agent to be administered to the subject is the therapeutically radioactive isotope, with the second or subsequent cycle of constant Sorafenib (or another multi-kinase inhibitor) dosing being initiated by administering a first dose of Sorafenib (or another multi-kinase inhibitor) within 24 hours, such as within 0.5, 1, 2, 4, 8, 12, 16, 20, or 24 hours of administering the dose of therapeutically radioactive isotope. On those days where both therapeutically radioactive isotope and Sorafenib (or another multi-kinase inhibitor) are scheduled to be administered to the subject, these therapeutic agents can be administered either at the same time (i.e., simultaneous administration) or at different times (i.e., sequential administration, in either order). In one such embodiment, the dose of therapeutically radioactive isotope is administered first, followed by administration of the dose of Sorafenib (or another multi-kinase inhibitor) within about 10 minutes to about 4 hours of the completion of administering the dose of therapeutically radioactive isotope, such as within about 10, 15, 20, 25, 30, 45, 60, 90, 120, 150, 180, 210, or 240 minutes.

Where concurrent therapy with Sorafenib (or another multi-kinase inhibitor) and therapeutically radioactive isotope comprises one or more cycles of Sorafenib (or another multi-kinase inhibitor) dosing regimen, the initial therapeutic agent to be administered to the subject at the start of a treatment period can be either Sorafenib (or another multi-kinase inhibitor) or therapeutically effective dose of the radioactive isotope, so long as the subject has an overlapping period of time during which both therapeutic agents are being administered to the subject, each according to the particular dosing regimen disclosed.

Thus, in one embodiment, concurrent therapy with these two therapeutic agents comprises initiating the two-level Sorafenib (or another multi-kinase inhibitor) dosing regimen prior to initiating administration of therapeutically effective doses of the radioactive isotope, where a therapeutically effective dose of the isotope is administered according to a weekly dosing schedule, or, alternatively, once every two, three, four or eight weeks. In this manner, a first dose of Sorafenib (or another multi-kinase inhibitor) is administered up to one month before the first dose of therapeutically radioactive isotope is administered.

In other embodiments, the two-level Sorafenib (or another multi-kinase inhibitor) dosing regimen and therapeutically radioactive isotope administration begin concurrently on the same day, either at the same time (i.e., simultaneous administration) or at different times (i.e., sequential administration, in either order). Thus, in another embodiment, in one embodiment where concurrent therapy with these two therapeutic agents begins on day 1 of a treatment period, a first therapeutically effective dose of therapeutically radioactive isotope and a first dose of Sorafenib (or another multi-kinase inhibitor)would both be administered on day 1 of this treatment period. In one such embodiment, the dose of therapeutically radioactive isotope is administered first, followed by administration of the dose of Sorafenib (or another multi-kinase inhibitor)within about 10 minutes to about 4 hours of the completion of administering the dose of therapeutically radioactive isotope, such as within about 10, 15, 20, 25, 30, 45, 60, 90, 120, 150, 180, 210, or 240 minutes.

In certain embodiments, a first therapeutically effective dose of radioactive isotope is administered to the subject, in another embodiment, on day 1 of a treatment period, and the two-level Sorafenib (or another multi-kinase inhibitor) dosing regimen is initiated by administering a first dose of Sorafenib (or another multi-kinase inhibitor) within 10 days of administering the first therapeutically effective dose of radioactive isotope. In such embodiments, the two-level Sorafenib (or another multi-kinase inhibitor) dosing regimen is initiated by administering a first dose of Sorafenib (or another multi-kinase inhibitor) within 7 days of administering the first therapeutically effective dose of the radioactive isotope, such as within 1 day in one embodiment, or 2, 3, 4, 5, 6, or 7 days in other discrete embodiments.

Depending upon the severity of the disease, the patient's health, and prior history of the patient's disease in certain embodiments, one or more cycles of Sorafenib (or another multi-kinase inhibitor) dosing regimen can be administered concurrently with the radioactive isotope therapy, where therapeutically effective doses of the isotope are administered weekly, or, alternatively, once every two, three, four or eight weeks.

In one embodiment, a therapeutically effective dose of the radioactive isotope is administered weekly, or is administered once every two, three, four or eight weeks, in combination with one or more cycles of a constant Sorafenib (or another multi-kinase inhibitor) dosing regimen or in combination with one or more cycles of therapeutically radioactive isotope dosing regimen. When a subject is undergoing concurrent therapy with these two therapeutic agents in the manner set forth herein, the duration of therapeutically radioactive isotope administration and the duration of any given cycle of either of Sorafenib (or another multi-kinase inhibitor) dosing regimens will depend upon the subject's overall health in one embodiment, or history of disease progression, and tolerance of the particular therapeutically radioactive isotope/Sorafenib administration protocol.

In another embodiment, therapeutically effective doses of the radioactive isotope are administered weekly (i.e., once a week), or once every two to eight weeks, such as in another embodiment, once every two weeks, once every three weeks, or once every four weeks, throughout a treatment period, where the treatment period includes one or more cycles of a constant Sorafenib (or another multi-kinase inhibitor) dosing regimen or one or more cycles of therapeutically effective radioactive isotope dosing regimen.

In one embodiment, the therapeutically effective radioactive isotope therapy can have a fixed duration within a treatment period. In this manner, a therapeutically effective dose of the radioactive isotope is administered weekly, or is administered once every two, three, four or eight weeks, for a fixed period of about 4 weeks to about 16 weeks, including 4, 5, 6, 7, 8, 9, 10, 11, 12, 13, 14, 15, or 16 weeks, in combination with one or more cycles of a constant Sorafenib (or another multi-kinase inhibitor) dosing regimen or in combination with one or more cycles of a two level-Sorafenib (or another multi-kinase inhibitor) dosing regimen. Thus, in another embodiment, where the isotope is administered weekly for a duration of 4 weeks or 8 weeks, the subject would receive four or eight therapeutically effective doses of the radioactive isotope, respectively, during concurrent therapy with Sorafenib (or another multi-kinase inhibitor). Similarly, where the isotope is administered once every two weeks for a duration of 4 weeks or 8 weeks, in another embodiment, the subject would receive two or four therapeutically effective doses of the radioactive isotope, respectively, during concurrent therapy with Sorafenib (or another multi-kinase inhibitor). Where the isotope is administered once every three weeks for a duration of 6 weeks, 9 weeks, 12 weeks, or 15 weeks, in another embodiment, the subject would receive two, three, four, or five therapeutically effective doses of the radioactive isotope, respectively, during concurrent therapy with Sorafenib (or another multi-kinase inhibitor). Similarly, where the isotope is administered once every four weeks for a duration of 8 weeks, 12 weeks, or 16 weeks, the subject would receive two, three, or four therapeutically effective doses of the radioactive isotope, respectively, during concurrent therapy with Sorafenib (or another multi-kinase inhibitor).

The duration of Sorafenib (or another multi-kinase inhibitor) administration during concurrent therapy with these two therapeutic agents is a function of Sorafenib (or another multi-kinase inhibitor) dosing regimen used. In another embodiment, Sorafenib (or another multi-kinase inhibitor) is administered according to the disclosed protocols, and a subject can repeat one or more cycles of a constant or two-level Sorafenib (or another multi-kinase inhibitor) dosing regimen as needed, unless Sorafenib toxicity symptoms develop. Should such toxicity symptoms develop, the subject can be taken off Sorafenib (or another multi-kinase inhibitor) dosing until complete resolution of any observed toxicity symptoms. Such toxicity responses include but are not limited to, Rash, Hand-foot syndrome (Palmar-plantar erythrodysesthesia or PPE)—skin rash, swelling, redness, pain and/or peeling of the skin on the palms of hands and soles of feet, diarrhea, Fatigue, High blood pressure, Hair loss (i.e. thinning or patchy hair loss), Nausea, Itching, Low white blood cell count, Poor appetite, Vomiting, Bleeding, Increased amylase/lipase blood counts, Low phosphorus level, Constipation, Shortness of breath, Cough, Numbness, tingling or pain in hands and feet, Low platelet count, Dry skin, Abdominal pain, Bone, muscle, joint pain, Headache, Weight loss, or heart attack and their combination. The subject may resume concurrent therapy with these two therapeutic agents as needed following resolution of signs and symptoms of these Sorafenib toxicity symptoms. Resumption of concurrent therapy with these two therapeutic agents can entail either of the therapeutically effective radioactive isotope/Sorafenib (or another multi-kinase inhibitor) administration protocols disclosed herein (i.e., therapeutically effective radioactive isotope with the constant Sorafenib (or another multi-kinase inhibitor) dosing regimen or therapeutically effective radioactive isotope with the two-level Sorafenib (or another multi-kinase inhibitor) dosing regimen), depending upon the overall health of the subject, relevant disease state, and tolerance for the particular therapeutically effective radioactive isotope/Sorafenib (or another multi-kinase inhibitor) administration protocol.

EXAMPLES

Materials and Experimental Methods

Patients

Eligible patients were >18 years old with metastatic or unresectable thyroid carcinoma for which curative measures were no longer effective. Patients had evidence of measurable disease by RECIST criteria. All patients enrolled had evidence of disease progression in the year prior to initiation of treatment. Prior radioactive iodine treatments and one prior biologic treatment (kinase inhibitor, vaccine or antibody-based therapy) were allowed, but not within 3 weeks of treatment. Other eligibility criteria included ECOG performance status <2; life expectancy >3 months; leukocyte count >3,000/uL, absolute neutrophil count (ANC) >1,500/mm3, platelets >100,000/mm3, hemoglobin >9 g/dl, serum creatinine <1.5 times upper limit of normal (ULN) or 24-hour creatinine clearance >75 cc/min, serum bilirubin <1.5 times ULN, serum glutamyloxaloacetic transaminase (SGOT) <2.5 ULN, alkaline phosphatase <2.5 times ULN, and PT-INR/PTT <1.5 times ULN. Pre-menopausal women were required to have a negative pregnancy test and all patients of were required to use contraception.

Patients were ineligible if they had previous exposure to a Ras pathway inhibitor (including trastuzumab, EGFR inhibitors, farnesyl transferase inhibitors or MEK inhibitors) or were unable to swallow and retain oral pills. All patients provided written informed consent prior to enrollment on the trial. The study protocol was approved by the Institutional Review Board of the University of Pennsylvania.

Study Design

This was an open-label, single institution phase II study of oral sorafenib in patients with metastatic thyroid carcinoma, including differentiated, poorly differentiated, medullary, and anaplastic subtypes. Sorafenib was administered at a dose of 400 mg orally twice a day. A cycle was defined as 4 weeks. Screening evaluations were completed within 2 weeks prior to the start of study drug, including medical history, demography, review of prior treatment, physical exam, 12-lead EKG, and laboratory evaluations including serum thyroid stimulating hormone (TSH) and thyroglobulin, and urinalysis. Radiological tests to identify target lesions were performed within 4 weeks of the first dose of study drug.

After beginning treatment, patients were followed at four-week intervals. At each visit, a history and physical examination were performed, and a CBC, chemistry panel, TSH and thyroglobulin drawn. Patients were assessed for new symptoms, compliance with study medications (pill count), and concomitant medications. Dose adjustments were made as needed for toxicity. Response was assessed radiographically after eight and sixteen weeks of treatment and every twelve weeks thereafter.

Study Endpoints

The study endpoints of best objective response rate and stable disease were measured based on the findings on computed tomography (CT) or magnetic resonance imaging (MRI) using RECIST. Additional endpoints included best response, duration of response and time to disease progression (TTP) on the basis of RECIST, clinical progression, or death. While TTP was the original endpoint, PFS and TTP were identical in this study, and PFS have been used in this report as it has become the more standard progression endpoint. All responses were confirmed by a study-designated radiologist. Adverse events were graded with the use of Common Terminology Criteria for Adverse Events, version 3.0 (CTCAE v3.0).

Statistical Analysis

This study was designed to exclude the null hypothesis response rate of 5% using a Simon two-stage design; the first stage included 30 patients, with an optional second stage including 25 additional patients if at least one response was observed. The observed response rate was tested against the null rate of 5% using an exact test for binomial proportions. Estimates of PFS (time from beginning on study drug to earlier of progression or death) with associated 95% confidence intervals were obtained using the method of Kaplan and Meier. Comparison of PFS among histological subtypes was conducted using the logrank test. All enrolled patients who received at least one day of treatment were included in this intent-to-treat analysis.

Example 1

Baseline Characteristics

Baseline characteristics of the patients entered on study are listed in Table 1; five patients had received prior chemotherapy. No patient was previously treated with a kinase inhibitor. All patients had progressive disease on baseline scans prior to the initiation of treatment and almost all (93%) of the patients had uptake of fluorodeoxyglucose on positron emission tomography (FDG-PET positive).

TABLE 1

Baseline Patient Characteristics

| Total Patients | 30 |
|---|---|
| Sex | |
| Male | 15 (50%) |
| Female | 15 (50%) |
| Mean Age (years) | 63 |
| Range | 31-89 |
| Baseline Performance Status (ECOG) | |
| 0 | 19 (63%) |
| 1 | 11 (37%) |
| Thyroid Cancer Subtype | |
| Papillary | 18 (60%) |
| Follicular/Hurthle Cell Variant | 9 (30%) |
| Medullary | 1 (3%) |
| Poorly differentiated/Anaplastic | 2 (7%) |
| Prior Surgery | 30 (100%) |
| Prior I-131 Treatment | 28 (93%) |
| Prior treatment | 5 (17%) |
| Prior chemotherapy | 3 (10%) |
| Prior investigational agents | 2 (7) |
| Prior external beam radiation | 11 (37%) |
| Prior FDG-PET | |
| FDG-PET scan completed | 29 (97%) |
| FDG-uptake positive (%) | 28 (93%) |

Example 2

Treatment Efficacy

Figure 1:
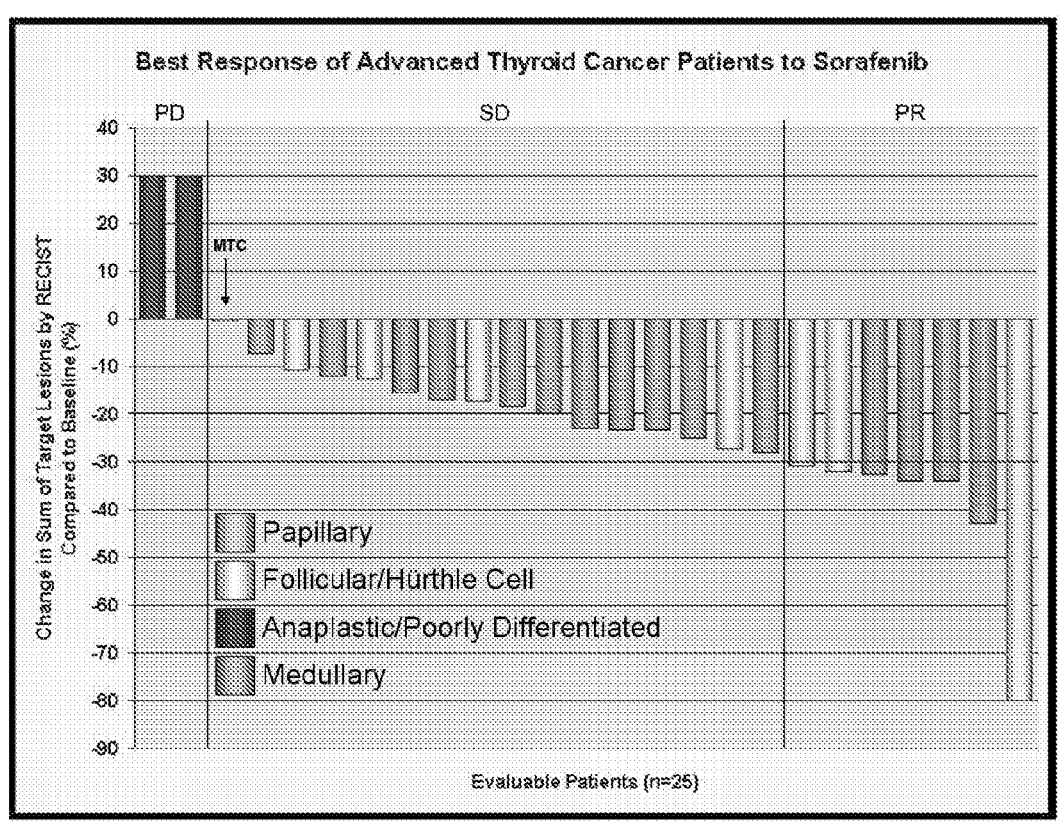
FIG. 1 shows best overall percentage of change from baseline in target lesion measurement. Baseline radiographic measurements of target lesions were compared with measurements over the course of the study to determine the best change in target lesion size for each patient with data.
Figure 2:
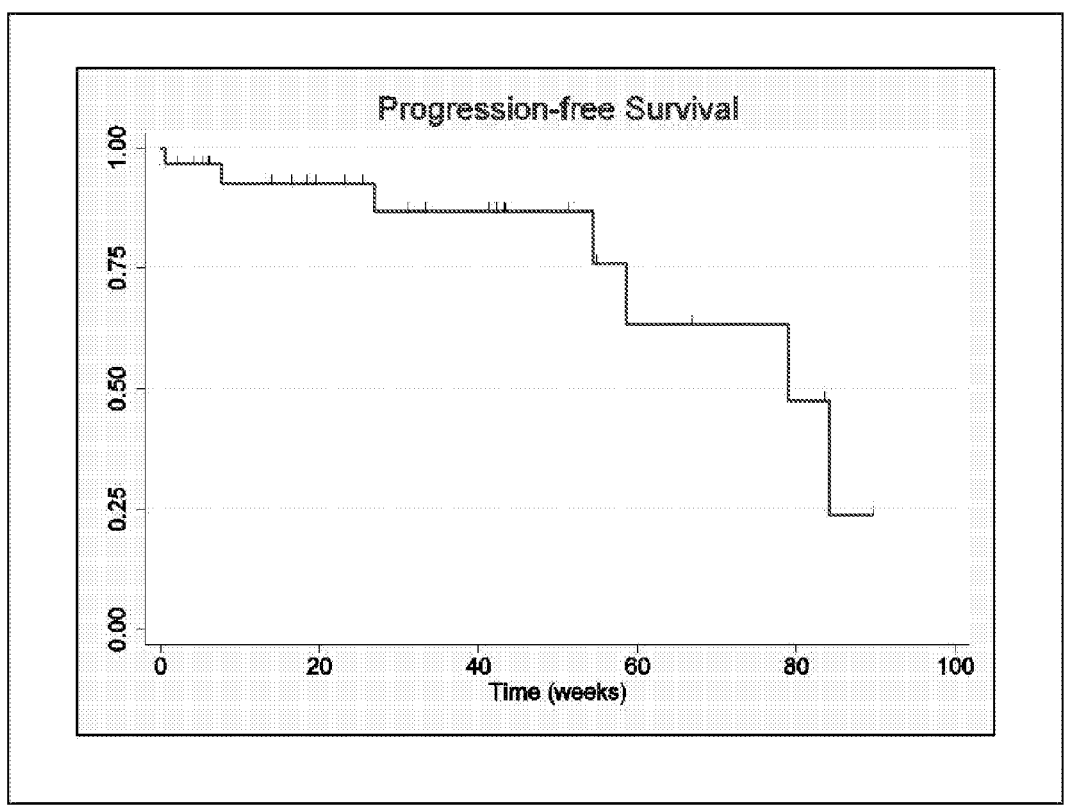
FIG. 2 shows Kaplan-Meier estimate of progression-free survival for patients on study. Median PFS was 79.0 weeks.

The best responses among the 30 patients were assessed (Table 2). This analysis was conducted four months after the last patient started treatment. Twenty-five patients were evaluable for response, but all 30 are included in this intention-to-treat analysis. Responses ranged from progressive disease to a decrease in target lesions of 80% by RECIST criteria (see FIG. 1). The objective partial response rate (defined as decrease in sum of longest diameter measurements >30% by RECIST) for patients on study was 23% (7 patients). The exact binomial 95% confidence interval (CI) of (0.10, 0.42) excludes the null hypothesis (p=0.0005). The stable disease rate (defined as change in sum of longest diameter measurements between −30% and +20% by RECIST) was 53% (16 patients; 95% CI (0.34, 0.72)). FIG. 2 shows the Kaplan-Meier curve for all 30 patients; the median overall PFS was 79 weeks. Analysis of differentiated thyroid cancers alone revealed a median PFS of 84 weeks. No patient died prior to progressing and no significant differences in PFS were observed between follicular and papillary subtypes. Seventeen of 19 patients (95%) on whom serial serum thyroglobulin levels are available showed a marked response in thyroglobulin levels with a mean decrease of 70% within four months of starting treatment.

TABLE 2

Patient Response

| Total patients (n) | 30 |
|---|---|
| Total evaluable patients | 25 (83%) |
| Best response by RECIST (n) | |
| Complete response | 0 (0%) |
| Partial response (PR, ≥30%) | 7 (23%) |
| Stable disease (SD) | 16 (53%) |
| Clinical benefit (PR + SD) | 23 (77%) |
| Progressive disease | 2 (3%) |
| Overall Median Progression Free Survival (weeks) | 79 |
| DTC Patients Median Progression Free Survival (weeks) | 84 |

Two patients, with histologically proven poorly differentiated and anaplastic disease, had progressive disease as their best response. Of note, the patient with poorly differentiated thyroid cancer had a visible nodule on his shoulder decreased in size by 50% at 4 weeks prior to progressing with new and enlarging pericardial lymph nodes on CT after 7 weeks of treatment. The patient with anaplastic carcinoma had medical complications and rapid clinical progression of her disease within 4 days of beginning sorafenib and was forced to discontinue treatment. Of the 30 patients, 5 withdrew from the clinical trial prior to two months on study; no imaging response data were available for these patients. Three of these patients withdrew due to toxicity, including one with a grade 3 rash, one due to exacerbation of a pre-existing cardiac condition, and one due to grade 2 fatigue. One patient had a complication related to radiation treatment of a non-target lesion, and one was non-compliant with the study drug. Four other patients on whom scans were available also withdrew. Of these, two patients withdrew due to toxicity from the study drug at 14 and 16 weeks: one patient with medullary thyroid cancer had grade 4 liver toxicity, and another had grade 2 fatigue. One patient with stable disease withdrew after 72 weeks due to pneumonia, resulting fatigue and subsequent decline in performance status, and another patient with stable disease was noncompliant with the study drug at 42 weeks.

Figure 3:
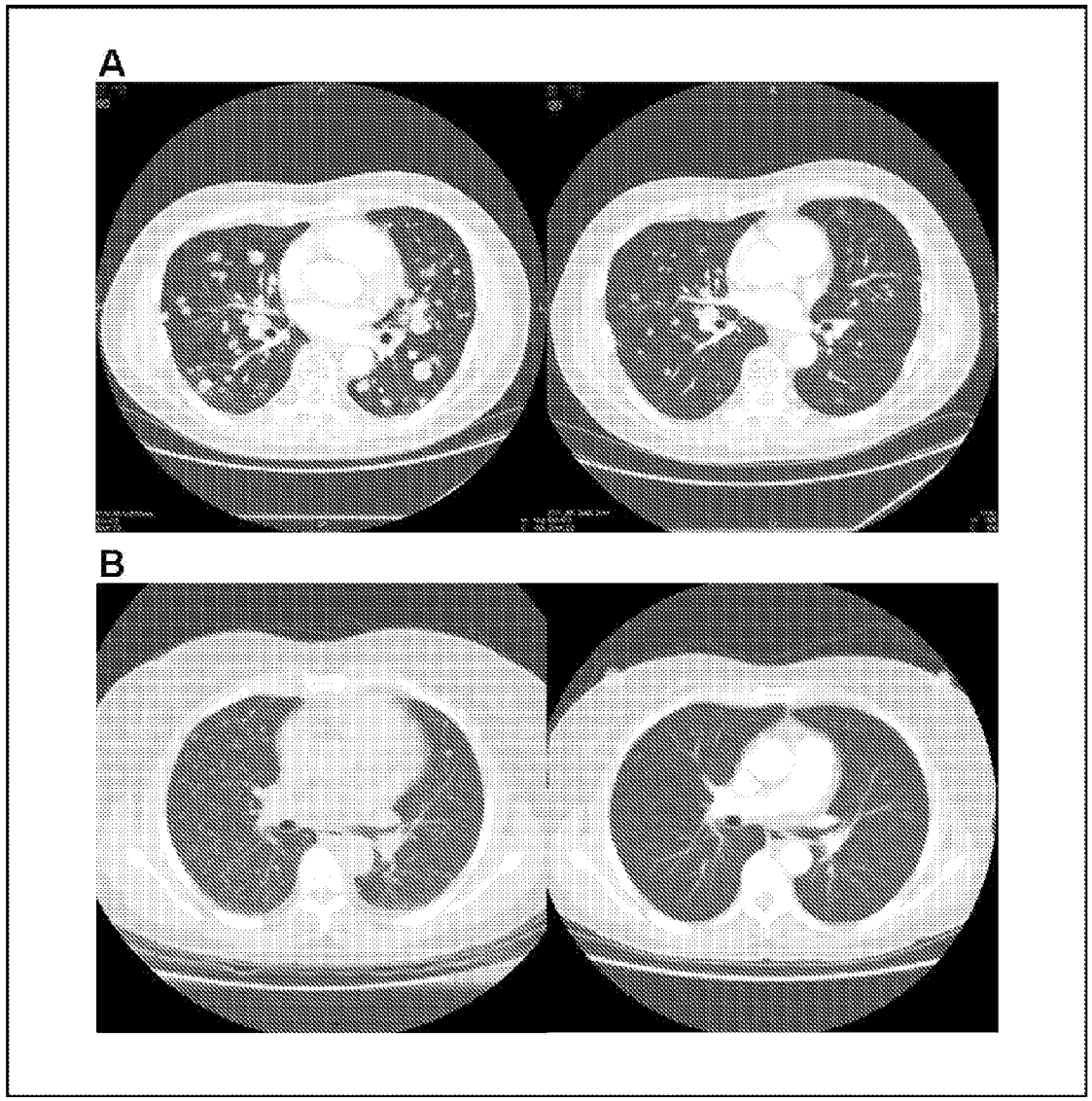
FIG. 3 shows that (A) a 60 year old man with follicular thyroid cancer had metastatic disease in the lung (left). Computed tomography scans confirm partial response in target lesions (right) after 16 weeks of treatment with sorafenib. (B) A 59 year old female with papillary thyroid cancer had widespread miliary lung metastases (left). CT scans show marked improvement in the burden of lung disease after 33 weeks of treatment with sorafenib (right).

The baseline and on-study scans are shown for two patients in FIG. 3. The first (FIG. 3A) had pulmonary metastasis which resulted in cough and dyspnea on exertion at the time of diagnosis of his primary thyroid cancer. The second patient (FIG. 3B) was diagnosed with papillary thyroid cancer and had undergone thyroidectomy three years prior when miliary spread of her thyroid cancer to the lung was discovered. Within a year the patient began to experience dyspnea on exertion. Both patients noted complete resolution of their symptoms within the first six months of treatment with sorafenib.

Phase II Study of Sorafenib in Patients with Metastatic Thyroid Carcinoma Primary Inclusion criteria: 1) Diagnosis of metastatic or unresectable thyroid carcinoma, for which curative or palliative measures do not exist or are no longer effective. 2) Evidence of measurable disease by RECIST criteria 3) Any number of prior radioactive iodine treatments and up to one prior biologic treatment.

Primary Endpoint: Efficacy of sorafenib (objective response rate) in patients with metastatic thyroid carcinoma.

Secondary Endpoints: 1) Characterize the in vivo effects of sorafenib on VEGFR and BRAF downstream signaling molecules in both the endothelial cell (EC) and tumor cell (TC) compartments. 2) Determine the relationship between clinical response to sorafenib and mutational status of BRAF. 3) Safety of sorafenib in patients with metastatic thyroid carcinoma. 4) Best response, time to disease progression, and duration of response in patients receiving sorafenib.

Study Design: Sorafenib 400 mg PO BID was administered daily. Patients on study were monitored with CT scans every 2 months and PET scans prior to beginning therapy and 4 weeks after starting treatment. Archival paraffin-embedded tumors from the primary surgery were genotyped for common mutation status.

Table 3: Below is a summary of the 41 patients who enrolled on the trial. PFS was estimated By Kaplan-Meier Analysis based on a follow-up to the interim analysis at 30 patients (FIG. 11).

The results show that Sorafenib has activity in metastatic thyroid cancer patients with a PR of 24% and clinical benefit rate of 72%. Moreover, Sorafenib leads to long term PFS of 84 weeks in patients with advanced differentiated thyroid cancer.

TABLE 3

Summary

| | |
|---|---|
| Total patients | 42 |
| Total evaluable patients | 31 |
| Screening error | 1 |
| Patients WD due to toxicity | 2 |
| Medical Issues (not drug related) | 3 |
| Enrolled <8 weeks | 4 |
| Scans not available | 1 |
| Response: | |
| Partial response (≥30%) | 10 (24%) |
| Stable disease | 19 (48%) |
| Clinical benefit (PR + SD) | 13 (72%) |
| Median time to progression of the first 30 patients as of May 25, 2008 | |
| All patients | 72 |
| Differentiated Thyroid Cancers (DTC) | 84 |

Since November 2008, approximately 15 new patients were enrolled. The results further confirmed the effect of sorafenib to increase iodine uptake in patients afflicted with iodine non-avid metastatic thyroid cancer. Thyroglobulin levels were measured periodically to monitor the response to therapy in patients being treated with radioactive iodine and/or sorafenib. Decreasing levels generally correlate with reduction in radioactive iodine uptake. Thyroglobulin levels increased in patients being treated with sorafenib. Thus, the results clearly show that sorafenib is effective in increasing the iodine uptake. The results further show that sorafenib is likely involved in reversing the differentiation process of thyroid cell and increasing the cell's ability to incorporate radioactive iodine.

Example 3

Adverse Events

The median duration of treatment was 27 weeks. Six patients (20%) discontinued treatment due to adverse events. Doses were reduced in 47% (14 patients) to control toxicities. For patients requiring dose reductions, sorafenib was decreased by 25% (to a total dose of 600 mg QD) initially, and 10 patients required up to 50% dose reductions (200 mg BID) for at least one period to control symptoms. Drug "holidays" were required due to adverse events in 63% of patients (19 patients). The duration of the dose interruptions ranged from one day to two weeks, with one patient requiring a three-week break due to musculoskeletal pain. Doses were interrupted most commonly due to fatigue, palmar/plantar erythema, rash, fatigue, stomatitis/mucositis, weight loss, and musculoskeletal pain.

Treatment-related adverse events were predominantly of grade 1 or 2, with the most common including palmar/plantar erythema, rash, fatigue, stomatitis/mucositis, weight loss, and musculoskeletal pain (Table 3). More severe toxicities observed included hypertension, rash, weight loss, diarrhea, palmar/plantar erythema, fatigue, pruritis, anorexia, anxiety and elevated lipase and amylase. One patient developed LFT elevations after eight weeks, and despite dose reductions and cessation of sorafenib per protocol, progressed and ultimately died of liver failure three months later. Symptoms of palmar/plantar erythema were successfully treated with anti-inflammatory agents, drug interruptions, and dosage reductions. 60% of patients (18 pts) experienced some weight loss. After the degree of weight loss was realized, nutrition counseling and supplementation were started earlier in the treatment course. In 6 cases, daily megestrol acetate (800 mg/day) was initiated to improve caloric intake.

Ten patients (33%) were referred to their primary endocrinologist for adjustments in their thyroid hormone replacement therapy due to a rise in serum TSH to levels greater than 0.10 mIU/L while on sorafenib. One patient had not established a baseline treatment dose prior to starting the trial, but the remaining 9 patients had been on a stable dose prior to beginning therapy.

Example 4

Evaluation of the Effect of Sorafenib on Tumor Vasculature and Iodine Metabolism in Vivo and ex Vivo Treatment with sorafenib can lead to elevation in sTG in the absence of progressive disease. Serum TG is used as a tumor marker in patients with metastatic thyroid cancer1, 7.

Figure 4:
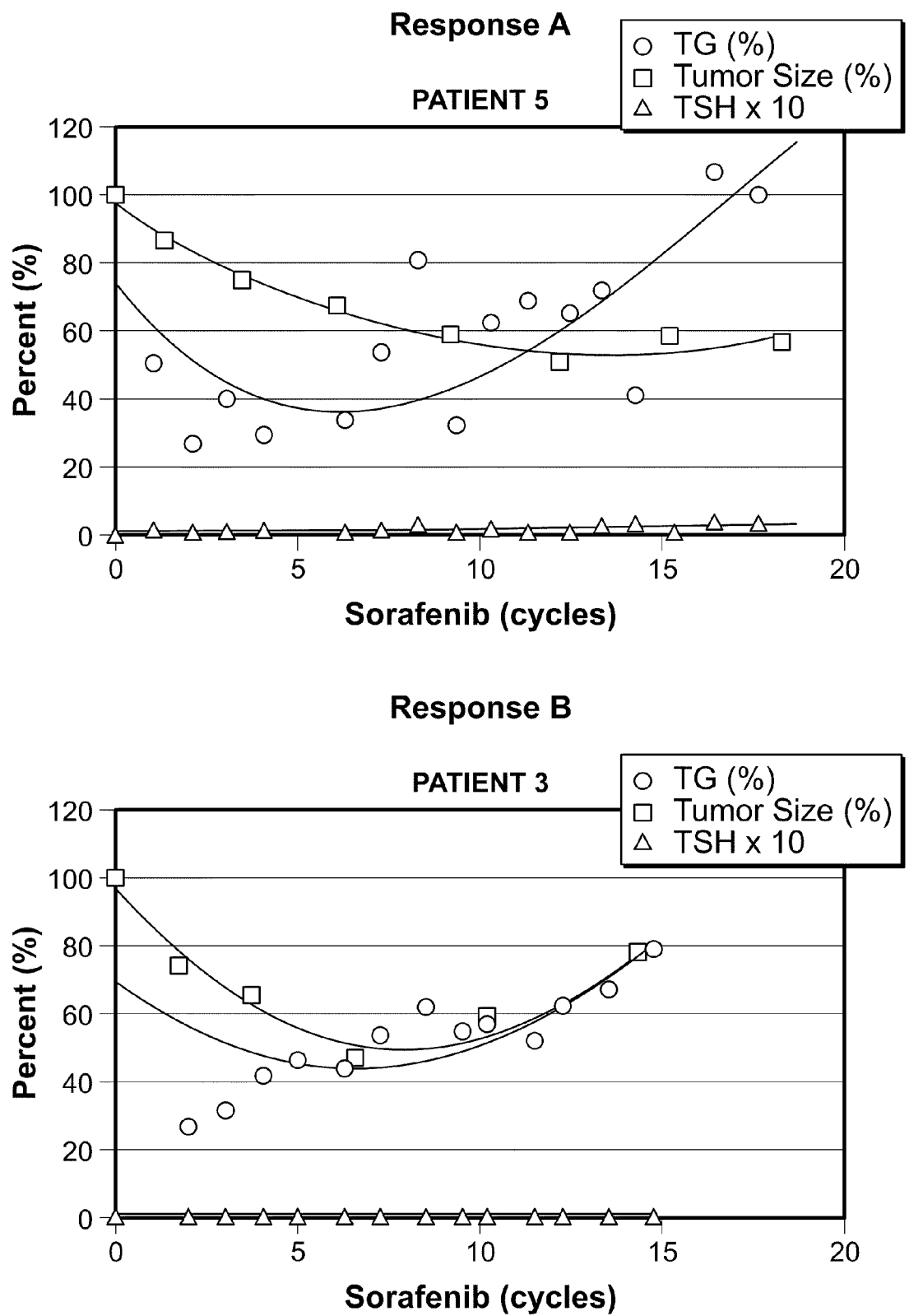
FIG. 4 shows Different Responses in patients on sorafenib with stably suppressed TSH. While patient 5 reached and maintained a PR in tumor size, serum thyroglobulin (sTG)

While some sub-types of differentiated thyroid cancer secrete only low levels of this marker, the vast majority of differentiated thyroid carcinoma (DTCs) can be followed in this manner. In most cases, the sTG reflects the disease burden and thus the amount of tumor cells. In order to correctly interpret the sTG, however, the TSH must be stably and adequately suppressed. Because of this, TSH was monitored in the patients on the clinical trial. It was noted that for most of the patients on the study, the sTG falls precipitously over the first two to four months (FIG. 4), and then begins to rise. While this heralded tumor growth in one case (FIG. 4, response B), it was not the true for all cases (FIG. 4, response A). Thus two discrete responses to sorafenib were observed. In Type A patients, the tumor shrinks, and stabilizes at a smaller size, while the sTG rises. In Type B patients, the sTG rise precedes and is accompanied by an increase in tumor size (See FIGS. 4A and B respectively). This effect can be related to the inhibition of RAF activity in these patients resulting in induction of iodine metabolizing genes. That this occurs in the setting of a treatment that is effective is an important finding. This observation may have significance not only in the prediction of outcomes for patients treated with sorafenib, but also for future treatment options. Thus, patients on sorafenib likely have an increase in their iodine uptake allowing them to be treated successfully with I-131 as part of combination or sequential therapy with sorafenib.

Example 5

In Vivo Imaging and STG Analysis of Patients on the Clinical Trial: DCE-MRI

DCE-MRI

Imaging Studies DCE-MRI take place under the IRB approved protocol UPCC 09202 prior to therapy, at two to four weeks after the initial cycle, and for selected patients that respond, they are studied following stabilization of the response (defined by two CT scans within 5% of each other by RECIST criteria) to document late perfusion changes and durability of response.

DCE-MRI takes place on a Siemens Sonata whole-body 1.5 T scanner equipped with 40 mT/m, 200 T/m/s gradients and torso/spine RF coil array. For each cohort, the DCE-MRI will include a 3-plane localizer scan followed by axial T1 and T2 images to aid in tumor localization prior to gadolinium administration. Prior imaging results (CT or MRI) can be used in reference to the pre-gadolinium imaging to determine lesion location. In the setting of multiple tumors, the dominant or largest lesion are identified for DCE-MRI evaluation. An appropriate oblique coronal volume is prescribed about the lesion to include the aorta in the field-of-view. This prescription volume will remain the same for subsequent T1 mapping (described below) and DCE-MRI. The DCE-MRI imaging will proceed with bolus injection of 0.1 mmol/kg Gd contrast (Omniscan©, Nycomed Imaging, Oslo, Norway) at 1 cc/sec using an infusion pump that is synchronized with the scanner, followed by a 20 cc saline flush. The injection rate is chosen so as to ensure that the peak arterial gadolinium concentration can be adequately quantified with the proposed imaging parameters. Injection begins after the acquisition of the 10th pre-contrast full data set and continues for a total of 8 minutes after contrast administration. The scans are performed during free-breathing. All attempts are made to use identical imaging geometries and IV sites at each of the two patient visits. Following the measurement of baseline T1, the gadolinium concentration curve is computed from the tumor signal enhancement kinetics. The data is then fit to Tofts' model98, and the parameters Ktr and estimation is dine using the Simplex method by minimizing the mean square difference between the data and the model. An estimated relaxivity r1 of Gad=4.5 mM-1 sec-199 and blood T1 of 1200 ms100 is used. The DCE-MRI parameters are evaluated at each pixel within the tumor, and pixels lacking adequate enhancement or demonstrating poor goodness of fit is discarded. For the remaining pixels median DCEMRI parameter values are obtained at each time point.

FDG-PET

FDG-PET and $^{124}$I-PET imaging studies. FDG-PET/CT studies are carried out per standard procedure followed at the University of Pennsylvania. To optimize patient throughput, patients receive 5 mCi $^{124}$I orally immediately after the FDG PET/CT has been carried out, and the I-124 PET/CT is obtained 2 days later (3 minutes per bed position, approximately 6-10 bed positions per patient). Respiratory gating is employed to accurately assess patients with lung lesions. Reconstruction are carried out using time of flight methodology developed at the University of Pennsylvania and uptake of $^{124}$I in tumor is measured using quantitative parameters. Imaging parameters including dose of radioactivity, image acquisition initiation time and reconstruction methodology, are kept identical for the baseline and post-therapy studies. I-124 is used under a Drug Master File that is cross-referenced from IBA-M (IRB protocol pending).

Serum sTG Analysis sTG levels are monitored monthly as part of the clinical trial. As sTG can rise due inadequate suppression of TSH, sTG levels are analyzed in the context of the serum TSH. In patients where sTG is not stably maintained below. In addition, high levels of anti sTG antibodies can render the sTG levels un-interpretable. To date one patient has TSH that was not adequately controlled, and a second patient with anti sTG antibodies in excess of 1000 IU/ml. These patients are excluded from this analysis. sTG levels are correlated with clinical outcomes, and results of imaging and tissue analysis as described in the section on statistical analysis below.

Until now, there has been no effective therapy for metastatic thyroid cancer that is not amenable to surgery and that does not concentrate iodine. Response rates with chemotherapy have been so low that best supportive care has been the standard of care for most patients. The results presented suggest the utility of using newer targeted therapies in treating metastatic thyroid cancer. Sorafenib is the only targeted therapy that targets both VEGFR and BRAF signaling.

As is evident on the CT scan in FIG. 3B, treatment with sorafenib resulted in a vast improvement in tumor burden in the lung, but since sub-centimeter lesions are considered non-measurable by RECIST criteria, improvement of this kind is not captured in the present overall response rate and points to the need for measures of disease-related symptoms and clinical benefit in future studies Although all subtypes of thyroid cancer were included in the present study, the patient population consisted mostly of patients with differentiated thyroid cancer; 27 of 30 patients had either papillary or follicular subtypes. Notably, the two patients who had progressive disease as their best response had poorly differentiated/anaplastic disease.

Serum thyroglobulin, a key tumor marker for differentiated thyroid cancers, dropped precipitously in patients receiving sorafenib. The decrease preceded tumor shrinkage on CT, and therefore reflects a biologic response in addition to decreased tumor burden Secretion of thyroglobulin is likely affected by alterations in cell signaling due to sorafenib.

In conclusion, long-term disease control in patients with advanced thyroid cancer can be obtained with sorafenib, a well-tolerated oral agent. Development of the multi-kinase inhibitors marks the first significant progress in treating patients with thyroid cancer in over 30 years. Treatment with sorafenib provided a clinical benefit (partial response+stable disease) rate of 77% in patients with iodine refractory, metastatic thyroid cancer in whom no other options for treatment are available. These promising results suggest that sorafenib warrants further investigation in the treatment of advanced thyroid cancer.

Example 6

In Vivo Activity of Sorafenib in Advanced Thyroid Cancer

Patients

Patient 1: An 84 year old male palpated a right-sided neck mass in August 2004. The patient underwent total thyroidectomy with lymph node dissection and pathology confirmed mPTC in one of eight lymph nodes. He was treated with $^{131}$I and placed on thyroid hormone replacement. In August 2005, an enlarged lymph node was palpated in his neck. An ultrasound revealed multiple enlarged nodes, and FDG-PET showed uptake in the neck and multiple pulmonary nodules. The patient was retreated with $^{131}$I, and his post-treatment scan revealed no evidence of residual disease. However, subsequent CT scans revealed progressing residual disease in the neck and chest.

The patient was referred to the Developmental Therapeutics Program at the University of Pennsylvania and was enrolled on a phase II trial of sorafenib in metastatic thyroid cancer. Treatment began on Apr. 18, 2006. Toxicity was assessed at every four weeks and response to treatment was assessed using serial CT and PET scans.

Patient 2: A 51 year old male presented with a sore throat in March 2002. His physician noted only right sided cervical lymphadenopathy. A fine needle aspiration of a lymph node revealed mPTC. Thyroidectomy and right neck lymph node dissection removed a 2.5 cm tall-cell PTC with 12 of 49 lymph nodes containing mPTC. Histology showed perineural invasion, extension into adjacent soft tissue and extrathyroidal vascular invasion. An iodine scan after surgery revealed uptake in the neck. The patient underwent $^{131}$I ablation, but post ablation imaging revealed continued uptake and his thyroglobulin level had markedly increased. A chest CT in June 2002 showed innumerable sub-centimeter pulmonary nodules bilaterally and serial CT scans showed progressive disease. In October 2003, he had a single lung lesion that measured 3.6 cm in maximum dimension, numerous smaller pulmonary nodules, and his disease was PET positive (FIG. 7). Clinically he was asymptomatic.

Methods

Immunohistochemistry

Paraffin embedded tumor specimens from the patients' primary surgery and from lymph node biopsies after two weeks (Patient 1) and 17 months on treatment (Patient 2) were obtained. Thin (5 µm) sections from tumor tissue were cut and stained for the proliferation marker Ki-67 (Dakocytomation), and signaling markers p-ERK and p-AKT (Cell Signaling Technology) which are downstream indicators of BRAF and VEGFR2 activity. P-ERK is good reporter for BRAF activity, while p-AKT likely reflects signaling through several pathways including VEGFR. Slides were counterstained with hematoxylin and mounted in vectashield (Vector Labs). Two independent, blinded pathologists scored the slides based on intensity of stain and percent of cells staining positively.

DNA Isolation and Sequencing

Tissue was macrodissected from 15 µM sections and genomic DNA was isolated as described previously. BRAF exon 15 was amplified by polymerase chain reaction (PCR), the amplified products were run on an agarose gel, purified using QIAquick Gel Extraction Kit (Qiagen) and analyzed on an ABI PRISM 3730 Sequence Analyzer (Applied Biosystems) using Sanger sequencing.

PET Scans

PET scans were obtained on a dedicated whole-body PET scanner (C-PET, Phillips). At FDG injection, patients had fasted for 6 hours and blood glucose levels were less than 150 mg/dL. Image acquisition started 60 min following intravenous administration of FDG at a dose of 1.85 MBq/kg (0.05 mCi/kg) body weight. A transmission scan was obtained for attenuation correction.

Evaluation of Response by CT and PET Scan

Patient 1: After 12 weeks of treatment the lesions in the lungs had decreased in size by 25% using RECIST criteria. After 12 months, the patient achieved apartial response (PR) with a decrease of 30% of the target lesions. All lung lesions and a right-sided cervical lymph node showed metabolic activity on the baseline PET scan. PET scans obtained three and seven weeks after starting treatment showed marked decrease in metabolic activity. The patient remains progression free at 1.3 years.

Patient 2: After 12 weeks of treatment, Patient 2's largest target lesion had decreased in size from 3.6 cm to 1.3 cm (52% decrease). All of the sub-centimeter lung nodules were smaller and some were no longer visible (Data not shown). A CT scan at 20 weeks confirmed the PR by RECIST. His largest target lesion continued to shrink to 1.0 cm (72% decrease) and his numerous small lung lesions have regressed further in size and number. After 3.7 years on sorafenib, he has not developed any new lesions and has maintained his 70% PR.

PET and CT scans obtained prior to beginning therapy and after one year of sorafenib treatment are shown in FIG. 8. A pre-treatment CT scan shows right and left lobe lung lesions with marked metabolic activity seen on PET (Data not shown), along with multiple other smaller nodules (FIG. 7a, arrowheads). Post-treatment scans reveal the lung nodules to be reduced in size and metabolic activity (FIG. 7d-e). Many of the smaller lesions have decreased in size or are no longer visible (FIG. 7d, arrowhead).

Histological and Molecular Findings

Proliferation and cellular signaling in the tumor cell (TC) and the endothelial cell (EC) compartments were evaluated by immunohistochemistry (IHC).

Patient 1: By IHC, 1% of TCs in pre-treatment tissue were strongly positive for Ki-67. Tissue obtained after two weeks of treatment showed less than 1% Ki-67 positive cells (FIGS. 8a and b). P-ERK and p-AKT were expressed in the ECs more than the TCs in pre-treatment tissue. After 2 weeks of treatment, p-ERK was no longer detected in the ECs and was decreased in the TCs (FIGS. 8c and d). P-AKT did not show any change after treatment in the TCs, but was decreased in the ECs (FIGS. 8e and f). The genotype of this tumor was found to be BRAF$^{wt}$ (FIG. 8g).

Patient 2: Up to 4% of TCs were strongly positive for Ki-67 prior to treatment, while tissue obtained after 17 months of treatment showed no change in the number of positive cells (FIGS. 9a and b). In pre-treatment samples, strong p-ERK staining was seen in the ECs, but variable p-ERK staining was seen in the TCs (FIG. 9c). In contrast, moderate p-AKT was observed in all TCs, and only a few ECs in pre-treatment samples (FIG. 9e). In tissue removed after 17 months of treatment, p-ERK staining appeared unchanged when compared to the pretreatment tissue in the TCs, but the ECs showed markedly increased p-ERK expression which was associated with a more rounded appearance of the endothelial cells (FIG. 9d). A slight increase in p-AKT staining was observed in the on-treatment sample in both the ECs and TCs at 17 months (FIG. 9f). This tumor was found to harbor the BRAF$^{V600E}$ mutation (FIG. 9g).

Rapidly progressing, iodine refractory mPTC which responded to treatment with sorafenib with a progression-free survival of 1.3+ and 3.7+ years respectively. Until now there has been no effective therapy for mPTC that is not amenable to surgery and which does not concentrate iodine. Response rates with chemotherapy have been so low that best supportive care has been the standard of care for most patients. In addition to inhibition of wild type and mutant (V600E) B-raf and C-raf kinase, this drug also inhibits VEGFR-2, VEGFR-3, PDGFR-β, Flt-3, c-KIT, and p38α.

The in vivo effects of sorafenib on downstream signaling markers of VEGFR and BRAF activity in both the EC and TC compartments in the two patients for whom serial tissue biopsies were available were characterized. In Patient 1, tumor tissue removed at two weeks had decreased in size and was grossly necrotic. IHC showed that p-ERK and p-AKT were primarily decreased in the ECs when compared to the TCs.

Slightly decreased Ki-67 staining at two weeks in Patient 1 suggests that sorafenib may lead to a decrease in tumor cell proliferation, although given the low Ki-67 rate prior to treatment this is difficult to quantitate. This finding correlates with a slight decrease in p-ERK staining in the TCs in the setting of relatively stable p-AKT. Thus, BRAF inhibition in the TCs may play a role in the response.

In Patient 2, sub-mandibular tumor tissue was removed at 17 months and studied using IHC. This tissue had been stable for several months on treatment and thus was resistant to sorafenib-mediated cell death. Both the ECs and some of the TCs in this tissue had either similar or stronger staining for p-ERK and p-AKT than in tissue removed prior to treatment.

Patient 2's tumor harbors the BRAF$^{V600E}$ mutation, while the tumor from Patient 1 is BRAF$^{wt}$ (FIGS. 8g and 9g). BRAF$^{V600E}$ results in constitutive activation of BRAF, thus leading to tumorigenesis. While the genotype of the tumor might be expected to affect the response of the TCs to sorafenib, endothelial cells in tumors are thought to be recruited from adjacent or circulating wild-type cells and thus would not be expected to harbor the mutation. Therefore, while BRAF/MEK/ERK cell signaling has been associated with aggressive subtypes of PTC, the BRAF$^{V600E}$ mutation would not lead to a difference in response to sorafenib if, as the data suggests, the primary effect of sorafenib is to target the endothelium.

Resistance to molecularly targeted agents is increasingly thought to be due to resistance in tumor stem cells which are biologically distinct from the more differentiated cells which constitute the majority of malignant cells. An initial period of clinical response to sorafenib associated with a decrease in downstream signaling in ECs and, to a lesser degree, TCs, as seen in Patient 1. Resistant cells, regardless of whether they are tumor stem cells, may permit the accumulation of secondary mutations which prevent sorafenib binding, leading to clinical progression in the future.

In conclusion, successful treatment of two patients with metastatic papillary thyroid carcinoma with sorafenib, along with correlative tissue studies in these patients is presented.

Example 7

DCE-MRI in Clinical Trials

Use of Combretastatin A4P (CA4P) on Solid Malignancies

The results in the CA4P trials were variable. In DCE-MRI, the rate constant Ktrans (Ktr), representing the rate of passage of gadolinium from the plasma into the tumor interstitium, is determined. Ktr itself is determined as a function of both tumor blood flow and vascular permeability, thus serving as a marker of the status of the tumor neovasculature. Strong Ktr responses to CA4P were noted in certain patients. These responses were seen almost exclusively those patients whose tumors demonstrated larger pre-treatment tumor Ktr values including two patients with thyroid cancer (one papillary and one medullary). In other patients, little or no effect was seen (FIG. 15).

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

What is claimed is:

1. A method of treating a thyroid cancer in a subject, comprising the step of enhancing iodine absorption in a thyroid in said subject by administering to said subject a composition comprising sorafenib and an mTOR inhibitor, and whereby said mTOR inhibitor is everolimus, tacrolimus, ABT-578, AP-23675, AP-23573, AP-23841, or combinations thereof, thereby treating said thyroid cancer in said subject.

2. The method of claim 1, whereby said thyroid cancer is differentiated metastatic thyroid cancer.

3. The method of claim 2, whereby said differentiated metastatic thyroid cancer is follicular or papillary differentiated metastatic thyroid cancer.

4. The method of claim 2, whereby the metastatic thyroid cancer is a remote metastatic thyroid cancer.

5. The method of claim 1, whereby the composition is administered after a primary thyroid cancer treatment.

6. The method of claim 5, whereby the primary thyroid cancer treatment is a radioactive iodine therapy.

7. The method of claim 5, whereby the primary thyroid cancer treatment comprises a surgery.

8. The method of claim 1, whereby the composition is administered before a thyroid cancer treatment.

9. The method of claim 8, whereby the thyroid cancer treatment is a radioactive iodine therapy.

10. The method of claim 8, whereby the thyroid cancer treatment comprises a surgery.

11. The method of claim 1, whereby said composition reverses the differentiation process of a cell in said thyroid and enhances said cell's ability to absorb iodine.

12. The method of claim 1, wherein said composition further comprises radioactive iodine.

13. The method of claim 12, whereby said radioactive iodine is $^{131}$I, $^{123}$I, $^{124}$I, $^{125}$I, $^{129}$I, or any combination thereof.

14. The method of claim 12, whereby the composition further comprises rosiglitazone.

15. The method of claim 12, whereby the composition further comprises one or more agents in addition to sorafenib and radioactive iodine.

16. The method of claim 15, whereby the agent is Sunitinib, Tanespimycin, KOS-953, 17-AAG, bortezomib, Vandetanib, Romidepsin, a histone deacetylase inhibitor, depsipeptide, gefitinib, irinotecan, AG-013736, lenalidomide, Belinostat, PXD101 or their combination.

17. The method of claim 15, whereby the agent inhibits VEGF-2, PDGF-α, PDGF-β, FLT-3, or c-KIT, and whereby the agent is selected from the group consisting of Bevacizumab, Imatinib, Leflunomide, Midostaurin, Semaxanib, Vatalanib, Recentin, AG013736, CDP860, CP547,632, CP673,451, RPI 4610, SU6668, VEGF-trap, ZD6474, YM359445, and combinations thereof.

18. The method of claim 12, whereby the agent inhibits the RAF/MEK/ERK pathway, and whereby the agent is CI-1040, ISIS 5132, or a combination thereof.

19. A method for providing a medical diagnostic or therapeutic procedure based on radioactive iodine in a subject, comprising the steps of: administering to said subject a composition comprising sorafenib, and performing a medical diagnostic or a therapeutic procedure on said subject, comprising administering to said subject said radioactive iodine concurrently with or subsequently to administration of said composition comprising sorafenib, wherein the medical diagnostic or therapeutic procedure based on radioactive iodine is used for the treatment or diagnosis of a bulky disease selected from the group consisting of non-Hodgkin's Lymphoma, a prostate adenocarcinoma, a breast cancer, and a liver cancer.

20. The method of claim 19, whereby said medical diagnostic procedure is a whole body scans (WBS).

21. The method of claim 19, whereby said composition comprising sorafenib further comprises said radioactive iodine.

22. The method of claim 21, whereby said radioactive iodine is $^{131}$I, $^{123}$I, $^{124}$I, $^{125}$I, $^{129}$I or any combination thereof.

23. The method of claim 19, whereby the composition further comprises one or more agents in addition to sorafenib.

24. The method of claim 23, whereby the agent is Sunitinib, Tanespimycin, KOS-953, 17-AAG, bortezomib, Vandetanib, Romidepsin, Rosiglitazone, a histone deacetylase inhibitor, depsipeptide, gefitinib, irinotecan, AG-013736, lenalidomide, Belinostat, PXD101 or their combination.

25. The method of claim 19, whereby the therapeutic procedure is radiotherapy, or radioimmunotherapy (RIT).

* * * * *

SEQUENCE LISTING

<160> NUMBER OF SEQ ID NOS: 2

<210> SEQ ID NO 1
<211> LENGTH: 15
<212> TYPE: DNA
<213> ORGANISM: Homo sapiens

<400> SEQUENCE: 1
acagtgaaat ctcga                                                     15

<210> SEQ ID NO 2
<211> LENGTH: 15
<212> TYPE: DNA
<213> ORGANISM: Homo sapiens

<400> SEQUENCE: 2
ctacagwgaa atctc                                                     15